(12) United States Patent
Soma et al.

(10) Patent No.: US 7,708,744 B2
(45) Date of Patent: *May 4, 2010

(54) DEVICE FOR INTRODUCTION OF LONG ITEM

(75) Inventors: Katsuaki Soma, Shizuoka (JP); Toshiaki Takagi, Shizuoka (JP); Hiroshi Yagi, Shizuoka (JP); Takayuki Mori, Shizuoka (JP); Katsuhiro Shirakawa, Shizuoka (JP); Hiraku Murayama, Shizuoka (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 110 days.

This patent is subject to a terminal disclaimer.

(21) Appl. No.: 12/003,331

(22) Filed: Dec. 21, 2007

(65) Prior Publication Data

US 2008/0114374 A1     May 15, 2008

Related U.S. Application Data

(63) Continuation of application No. 11/067,771, filed on Mar. 1, 2005, now Pat. No. 7,331,966.

(30) Foreign Application Priority Data

Mar. 1, 2004   (JP) .............................. 2004-056338
Mar. 9, 2004   (JP) .............................. 2004-065675
Mar. 11, 2004  (JP) .............................. 2004-069175

(51) Int. Cl.
*A61F 11/00* (2006.01)
(52) U.S. Cl. ....................... 606/108; 604/160
(58) Field of Classification Search ......... 604/158–161, 604/164.01, 164.04–164.05, 164.13; 606/108; 600/585

See application file for complete search history.

(56) References Cited

U.S. PATENT DOCUMENTS 3,611,965 A     10/1971   Lange (Continued)

FOREIGN PATENT DOCUMENTS

EP     0 554 754 A1     8/1993

(Continued)

OTHER PUBLICATIONS

Extended European Search Report issued in corresponding EP 07 02 3259, Feb. 29, 2008, EPO, Berlin, DE.

*Primary Examiner*—Nicholas D Lucchesi
*Assistant Examiner*—Theodore J Stigell
(74) *Attorney, Agent, or Firm*—Buchanan Ingersoll & Rooney PC

(57) ABSTRACT

A device (such as guidewire inserter) for easily and certainly inserting a medical long item having a curved tip into a tube such as catheter and sheath includes a tubular member having a bore for passage of a guidewire. The tubular member has a slit cutting across the wall over the total length of the tubular member. The proximal end of the tubular member has an aperture. The proximal end of the aperture has an open part and a connecting part adjacent thereto for the holder tube. There is a pair of wing-like protruded pieces projecting in the mutually opposite directions at both sides of the open part. The distal end of the tubular member has on its outer surface a pair of protruded rims, which project in the mutually opposite directions.

10 Claims, 23 Drawing Sheets

U.S. PATENT DOCUMENTS

| | | |
|---|---|---|
| 3,826,256 A | 7/1974 | Smith |
| 4,354,491 A * | 10/1982 | Marbry .................. 604/160 |
| 4,726,369 A | 2/1988 | Mar |
| 4,747,833 A | 5/1988 | Kousai et al. |
| 5,318,542 A | 6/1994 | Hirsch et al. |
| 5,395,335 A | 3/1995 | Jang |
| 5,397,311 A | 3/1995 | Walker et al. |
| 5,443,081 A | 8/1995 | Klosterman |
| 6,221,081 B1 | 4/2001 | Mikus et al. |
| 6,322,586 B1 | 11/2001 | Monroe et al. |
| 6,551,281 B1 | 4/2003 | Raulerson et al. |
| 7,331,966 B2 * | 2/2008 | Soma et al. .................. 606/108 |

FOREIGN PATENT DOCUMENTS

| | | |
|---|---|---|
| EP | 0 593 211 A2 | 4/1994 |
| EP | 0 807 447 A1 | 11/1997 |
| JP | 7-155382 A | 6/1995 |
| JP | 07155382 A * | 6/1995 |
| WO | 00/69500 A1 | 11/2000 |
| WO | 2004/066907 A3 | 8/2004 |

\* cited by examiner

DEVICE FOR INTRODUCTION OF LONG ITEM

This application is a continuation of application Ser. No. 11/067,771 filed on Mar. 1, 2005, now U.S. Pat. No. 7,331,966 B2, the entire content of which is incorporated herein by reference.

FIELD OF THE INVENTION

The present invention relates to a device for introduction of a long item for medical use, such as guidewire and catheter (the device will be referred to as inserter hereinafter).

BACKGROUND DISCUSSION

It has been common practice to use a guidewire inserter for introduction of a catheter guidewire (long item) into a puncture needle, catheter, or sheath.

The guidewire inserter is used to straighten a guidewire having a curved tip. It is a cylindrical body made up of a guidewire inlet at its proximal end, a guidewire outlet at its distal end, and a guidewire passage connecting the inlet and outlet. It is used in such a way that the guidewire outlet is brought into contact with the proximal end of the puncture needle, catheter, or sheath, and the guidewire is inserted into the guidewire inlet and then further inserted into the puncture needle, catheter, or sheath through the guidewire passage and the guidewire outlet.

The conventional guidewire inserter as mentioned above has the disadvantage of presenting difficulties in inserting into the inserter a guidewire having a curved tip. The guidewire is so curved as to fit to a specific part of blood vessel. Therefore, with the conventional guidewire inserter, it is difficult to inert a guidewire having a curved tip (in J shape, double-angle shape, or angle shape) into the inserter while straightening the curved tip.

In order to address this problem, in JP 7-155382 A, there has been proposed a guidewire inserter having a groove, which introduces the guidewire, at its proximal end (near the guidewire inlet). This groove has a V-shaped cross section whose width remains constant in the longitudinal direction of the guidewire inserter and changes in the thickness direction of the guidewire inserter.

However, the above-mentioned guidewire inserter having a groove at its proximal end does not permit the recent guidewire with a sharply curved J-shape tip to be inserted easily, with the curved tip being straightened.

The difficulty in inserting the guidewire into the opening of the rear end of the guidewire inserter may be solved by inserting the rear end of the guidewire into the distal end (or the guidewire outlet) of the guidewire inserter and then moving the guidewire inserter to the distal end of the guidewire. This procedure, however, takes a long time to move the guidewire inserter from the rear end to the distal end of a guidewire longer than 150 cm.

The above-mentioned problem is also involved with the angiography catheter, which needs a catheter inserter to straighten the curved tip at the time of insertion into the living body.

Another problem with the conventional guidewire inserter is that it is difficult to connect the distal end (or the guidewire outlet) of the guidewire inserter to the proximal end of the puncture needle, catheter, or sheath. The incomplete or misaligned connection prevents smooth insertion of the distal end of the guidewire, with its curved tip straightened.

During operation, it is often necessary to hold both the guidewire and the guidewire inserter with one hand. It is also necessary to hold both the guidewire and the guidewire inserter simultaneously in order to take out the guidewire from the container (or the holder tube) and insert it into the guidewire inserter. The conventional guidewire inserter prevents handling in such a way, with the result that only the guidewire inserter is pulled off from the holder tube.

SUMMARY

It is a first object of the present invention to provide a device for introduction of a long item. The device permits easy insertion of a medical long item with a curved tip while straightening the curved tip during insertion.

It is a second object of the present invention to provide a device for introduction of a long item. The device permits easy and adequate introduction of a medical long item with a curved tip into a puncture needle, catheter, or sheath.

It is a third object of the present invention to provide a device for introduction of a long item. The device permits easy insertion of a medical long item with a curved tip and also exhibits good handling properties such that the device can be held together with the medical long item simultaneously by one hand.

The present invention to achieve the above-mentioned objects is defined in the following paragraphs (1) to (38).

(1) A device for introduction of a long item for medical use, which is a tubular member having a bore for passage of a long item and which has a slit cutting across the wall thereof over the total length thereof, wherein the tubular member has a distal end which is constructed such that a part thereof in the circumferential direction projects in the distal direction and the slit cuts through the projecting part.

(2) The device for introduction of a long item as defined in paragraph (1), wherein the projecting part takes on a mountain-like shape having a vertex and slopes in its plan view, and the slit passes through the vertex or slope of the mountain-like shape.

(3) The device for introduction of a long item as defined in paragraphs (1) or (2), wherein the projecting part has a length no shorter than 1 mm, particularly 1 to 3 mm.

(4) The device for introduction of a long item as defined in any of paragraph (1) to (3), wherein the tubular member has at the proximal end thereof an aperture which results from the slit expanding toward the proximal end.

(5) The device for introduction of a long item as defined in paragraphs (4), wherein the aperture roughly takes on a V-shape.

(6) The device for introduction of a long item as defined in any of paragraphs (1) to (5), wherein d/Dmax is 0.2 to 2.0, where Dmax denotes the maximum apart distance of the aperture and d denotes the outside diameter of the long item.

(7) The device for introduction of a long item as defined in any of paragraphs (1) to (6), wherein the slit tightly closes at least partly across the thickness of the wall of the tubular member.

(8) The device for introduction of a long item as defined in any of paragraphs (1) to (7), wherein the tubular member has a part whose outside diameter gradually tapers in going from the proximal to the distal end.

(9) A device for introduction of a long item for medical use, which is a tubular member having a bore for passage of a long item, wherein the tubular member has a plurality of projections on the circumferential direction of the distal end thereof so that the distal end thereof is connected at the proximal end of a tube, with the projections coming into contact with the inside of the tube at the time of insertion.

(10) The device for introduction of a long item as defined in paragraph (9), wherein the projections are arranged at equi-angular intervals along the circumferential direction of the tubular member.

(11) The device for introduction of a long item as defined in paragraph (9) or (10), wherein the projections are protruded rims extending in the longitudinal direction of the tubular member.

(12) The device for introduction of a long item as defined in any of paragraphs (9) or (11), wherein the projections have the outermost surface which slopes with respect to the central axis of the tubular member.

(13) The device for introduction of a long item as defined in paragraph (12), wherein the slope has an angle of 0.5 to 45°.

(14) The device for introduction of a long item as defined in any of paragraphs (9) or (13), wherein the projections have the outermost surface which convexly curves.

(15) The device for introduction of a long item as defined in any of paragraphs (9) or (14), wherein the projections are integrally formed from a material which is identical with or different from the material of the tubular member.

(16) The device for introduction of a long item as defined in any of paragraphs (9) to (15), wherein the tubular member has at the proximal end thereof an open part at which the bore opens.

(17) The device for introduction of a long item as defined in any of paragraphs (9) to (16), wherein the tubular member has a slit, which extends in the longitudinal direction thereof and cuts across the wall thereof.

(18) The device for introduction of a long item as defined in paragraph (17), wherein the slit has at the proximal end thereof an aperture, which results from the width of the slit expanding toward the proximal end.

(19) The device for introduction of a long item as defined in paragraph (17), wherein the slit has at the proximal end thereof an aperture which results from the width of the slit expanding toward the proximal end and which has a roughly V-shaped aperture communicating with the open part.

(20) The device for introduction of a long item as defined in any of paragraphs (17) to (19), wherein the slit tightly closes at least partly across the thickness of the wall of the tubular member.

(21) The device for introduction of a long item as defined in any of paragraphs (17) to (20), wherein the projections are formed in pair in the opposite direction with respect to a plane containing the slit.

(22) The device for introduction of a long item as defined in any of paragraphs (9) to (21), wherein the projections have a function to prescribe the depth of insertion into the tube.

(23) The device for introduction of a long item as defined in any of paragraphs (9) to (22), wherein the projections have a function to align the tubular member and the tube with each other.

(24) The device for introduction of a long item as defined in any of paragraphs (9) to (23), wherein the tubular member has a part whose outside diameter gradually tapers in going from the proximal to the distal end.

(25) The device for introduction of a long item as defined in any of paragraphs (9) to (24), wherein the tubular member has at the proximal end thereof a connecting part capable of connection to the container holding the long item.

(26) A device for introduction of a long item for medical use, which is a tubular member having a bore for passage of a long item and which has a slit extending in the longitudinal direction thereof and cutting across the wall thereof, wherein the tubular member has at the proximal end thereof a pair of wing-like projections projecting in the mutually opposite directions.

(27) The device for introduction of a long item as defined in paragraph (26), wherein the projections assume a flat shape.

(28) The device for introduction of a long item as defined in paragraph (26), wherein the projections assume a shape having a curved part.

(29) The device for introduction of a long item as defined in paragraph (26), wherein the projections assume a shape having a flat part and a curved part.

(30) The device for introduction of a long item as defined in any of paragraphs (26) to (29), wherein the projections have a length in the longitudinal direction of the tubular member with 10 to 50% of the total length of the device for introduction of a long item.

(31) The device for introduction of a long item as defined in any of paragraphs (26) to (30), wherein the tubular member has at the proximal end thereof an open part at which the bore opens.

(32) The device for introduction of a long item as defined in paragraph (31), wherein the inner surface of the open part has a surface treatment to reduce friction.

(33) The device for introduction of a long item as defined in any of paragraph (31) or (32), wherein the region in which the open part is formed and the region in which the projections are formed overlap at least partly with each other in the longitudinal direction of the tubular member.

(34) The device for introduction of a long item as defined in any of paragraphs (26) to (33), wherein the slit has at the proximal end thereof an aperture which results from the width of the slit expanding toward the proximal end.

(35) The device for introduction of a long item as defined in any of paragraphs (31) to (33), wherein the slit has at the proximal end thereof an aperture which results from the width of the slit expanding toward the proximal end and which has a roughly V-shaped aperture communicating with the open part.

(36) The device for introduction of a long item as defined in any of paragraphs (26) to (35), wherein the slit tightly closes at least partly across the thickness of the wall of the tubular member.

(37) The device for introduction of a long item as defined in any of paragraphs (26) to (36), wherein the tubular member has a part whose outside diameter gradually tapers in going from the proximal to the distal end.

(38) The device for introduction of a long item as defined in any of paragraphs (26) to (37), wherein the tubular member has at the proximal end thereof a connecting part capable of connection to the container holding the long item.

The device according to the present invention makes it possible to easily insert a long item for medical use, such as guidewire and catheter with a curved tip, while straightening the curved tip or keeping the straight shape. Therefore, it permits easy and certain insertion of a long item for medical use having a curved tip into the bore of a puncture needle, catheter, or sheath.

The device according to the present invention makes it possible to easily and adequately connect the distal end of a long-item inserting device to the proximal end of a tube, such a puncture needle, catheter, and sheath. It also makes it possible to easily and certainly insert a medial long item having a curved tip into the tube from a long-item inserting device.

The device according to the present invention makes it possible to hold the medical long item and the long-item inserting device simultaneously by one hand. Therefore, it improves handling properties at the time of moving a medical long item to a long-item inserting device from a container of a medical long item or at the time of inserting a medical long item into the bore of a puncture needle, catheter, or sheath.

Consequently, the present invention contributes to rapid and adequate medical practice through easy insertion of a medical long item into the bore of a tube.

DETAILED DESCRIPTION OF THE PREFERRED EMBODIMENTS

The invention will be described in more detail with reference to the accompanying drawings.

First Embodiment

Figure 1:
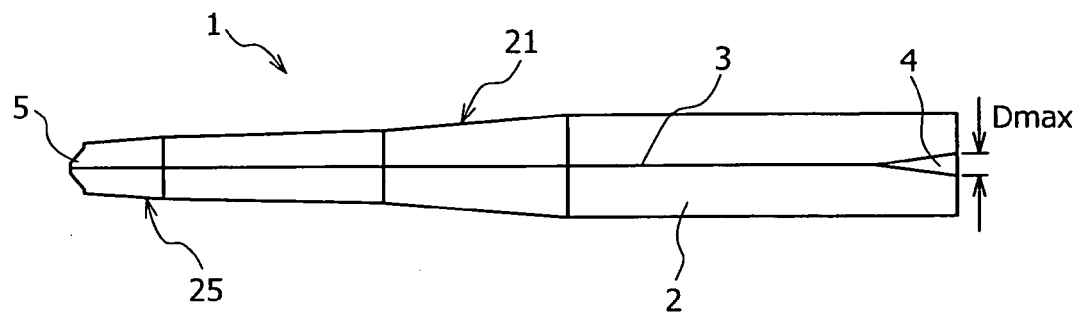
FIG. 1 is a plan view showing the device for introduction of a long item according to the first embodiment of the present invention, with the device being used as a guidewire inserter.
Figure 2:
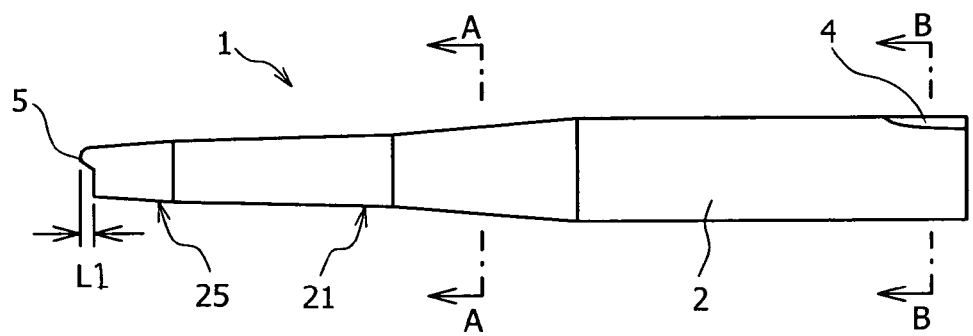
FIG. 2 is a side view of the guidewire inserter shown in FIG. 1.
Figure 3:
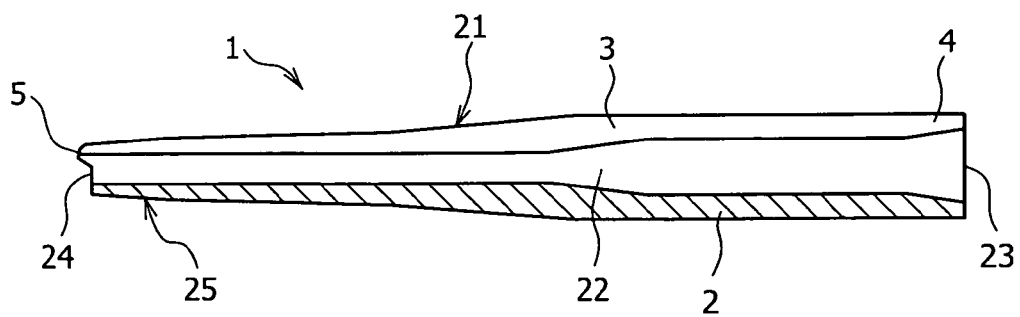
FIG. 3 is a sectional side view of the guidewire inserter shown in FIG. 1.
Figure 4:
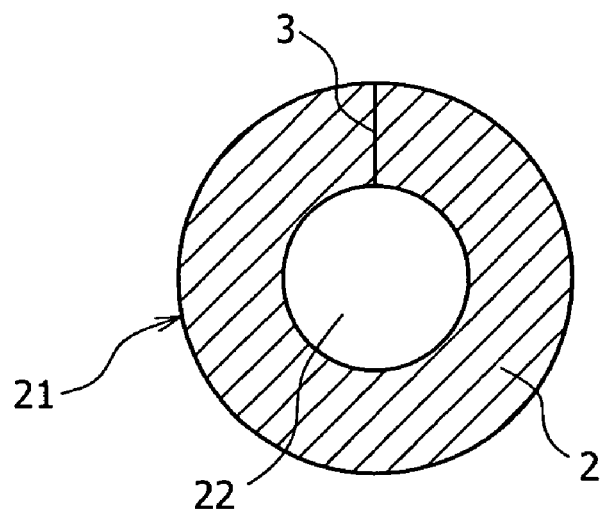
FIG. 4 is a sectional view taken along the line A-A in FIG. 2.
Figure 5:
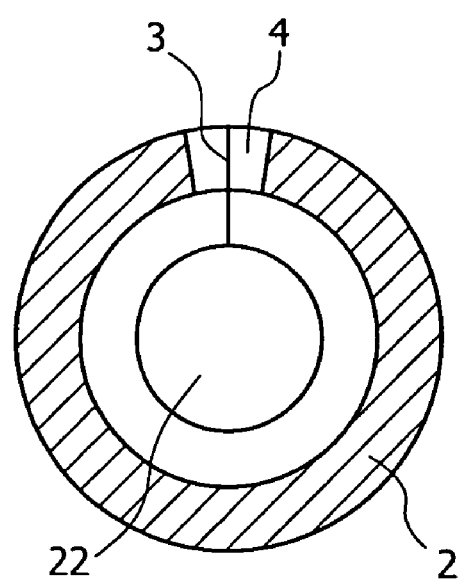
FIG. 5 is a sectional view taken along the line B-B in FIG. 2.

FIG. 1 is a plan view showing the device for introduction of a long item according to the first embodiment of the present invention. The device is used as a guidewire inserter. FIGS. 2 and 3 are a side view and a sectional side view, respectively, of the guidewire inserter shown in FIG. 1. FIG. 4 is a sectional view taken along the line A-A in FIG. 2. FIG. 5 is a sectional view taken along the line B-B in FIG. 2.

As shown in FIGS. 1 to 5, the guidewire inserter 1 is a tubular member 2 having a bore 22 (guidewire passage) inside that permits the guidewire, which is a medical long item, to pass through.

The tubular member 2 includes two parts: a cylindrical part (near the proximal end) having an approximately constant outside diameter, and a tapered part 21 having a decreasing outside diameter in going to the distal end. The tapered part 21 facilitates easy insertion of the guidewire inserter 1.

Incidentally, the tapered part 21 may be uniformly or stepwise tapered over its total length. (Refer to FIGS. 1 and 2.)

The distal end 25 of the tubular member 2 should preferably be tapered to its end. The distal end 25 is inserted into and connected to a puncture needle, a catheter, a hub of a catheter, a connector, or a sheath (not shown). It also straightens the curved tip of the guidewire. The tapered shape of the distal end 25 facilitates insertion and connection.

The bore 22 has its both ends opened at the proximal end and distal end of the tubular member 2. The opening at the proximal end of the tubular member 2 constitutes the inlet 23 for the guidewire. The opening at the distal end of the tubular member 2 constitutes the outlet 24 for the guidewire. The inlet 23 and outlet 24 may take on any shape (ellipse and polygon) although they are round in the figures.

The bore 22 does not necessarily have a constant inside diameter over its total length. The bore 22 shown in FIG. 3 has a larger inside diameter near the proximal end of the tubular member 2.

The inside diameter of the bore 22 should be large enough for the guidewire to pass through. To be concrete, it should preferably be 0.3 to 1.5 mm. For use as an inserter for an angiography catheter (mentioned later), the inside diameter should preferably be 0.3 to 2.5 mm, more preferably 0.4 to 2.2 mm.

The tubular member 2 may be made of a stiff but somewhat resilient material, such as polyolefin (polyethylene and polypropylene), polyamide, and polycarbonate.

The tubular member 2 has a slit 3 formed over its total length. The slit 3 penetrates the wall of the tubular member 2.

The slit 3 is straight in its plan view (FIG. 1) and is parallel to the central axis of the tubular member 2.

The slit 3 facilitates insertion of the guidewire because it opens when the guidewire is inserted into the bore 22 of the tubular member 2.

As shown in FIG. 4, the slit 3 has a straight cross section. In other words, it should tightly close over the entire distance from the bore 22 of the tubular member 2 to the outside of the tubular member 2. Alternatively, the slit 3 may have a Y- or V-shaped cross section, in which case it closes only at the bore side.

The slit 3 prevents the guidewire from escaping from the bore 22 unexpectedly after the guidewire has been inserted into the bore 22, because it tightly closes at least partly across the thickness of the wall.

The slit 3 gradually expands near the proximal end of the tubular member 2, thereby constituting an aperture 4, as shown in FIGS. 1 and 5. The aperture 4 takes on a V-shape in its plan view. The aperture 4 facilitates insertion of the guidewire into the bore 22, because it functions as a starting point for insertion. In other words, one who wants to insert the guidewire into the inserter may insert the guidewire into the aperture 4 and then push it into the bore 22. As the guidewire is pushed into the bore 22, the slit 3 opens such that opening gradually moves to the distal end.

In the illustrated constitution, the aperture 4 is most widely apart at the proximal end of the tubular member 2. The maximum apart distance (Dmax) of the aperture 4 is not specifically restricted; however, it should preferably be such that the ratio of d/Dmax (where d is the outside diameter of the guidewire) is about 0.2 to 2.0, preferably about 0.5 to 0.9. The aperture 4 specified above facilitates insertion of the guidewire into the slit 3 through the aperture 4.

The aperture 4 is not specifically restricted in its length in the longitudinal direction (or the longitudinal direction of the tubular member 2); however, it should be about 0.1 to 2.5 mm long, preferably about 0.1 to 3.0 mm long.

The tubular member 2 has a projection 5 at its distal end. This projection 5 is a distally projecting part of the circumferential direction of the tubular member 2. (This part is at the upper side in FIG. 2.) This projection 5 takes on a mountain-like shape, with a vertex and slopes, in its plan view (FIG. 1). The slit 3 passes through the vertex of the mountain-like shape of the projection 5. In other words, the projection 5 is symmetrical with respect to the slit 3. The projection may also be formed such that the slit 3 passes through the slope of the mountain-like shape.

The projection 5 contributes to strength and prevents the curved tip of the guidewire from being caught by the slit 3 when the curved tip is straightened at the distal end 25. Therefore, it facilitates straightening of the curved tip of the guidewire and also facilitates insertion of the guidewire into the puncture needle, catheter, or sheath.

The projection 5 is not specifically restricted in the projecting length L1 in the distal direction; however, the projecting length should preferably be no shorter than 1 mm, more preferably about 1 to 3 mm.

Incidentally, the embodiment with the projection 5 may be replaced by the other one in which the slit 3 parallel to the central axis of the tubular member 2 deviates from the central axis near the distal end 25. In this case, the slit 3 may be formed such that its direction is inclined 20 to 300 with respect to the central axis of the tubular member 2 at that part away from the distal end 25. The slit 3 formed in this manner prevents the curved tip from being caught by the slit 3 when the curved tip of the guidewire is straightened.

Second Embodiment

Figure 6:
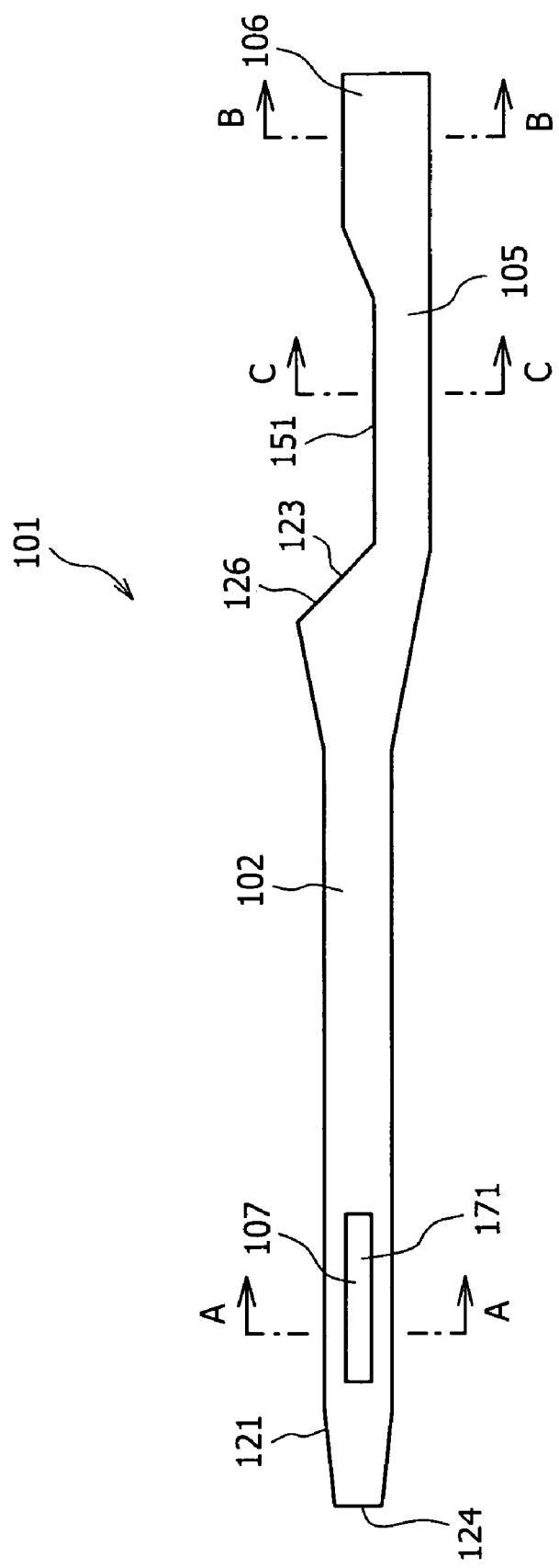
FIG. 6 is a side view showing the device for introduction of a long item according to the second embodiment of the present invention, with the device being used as a guidewire inserter.
Figure 7:
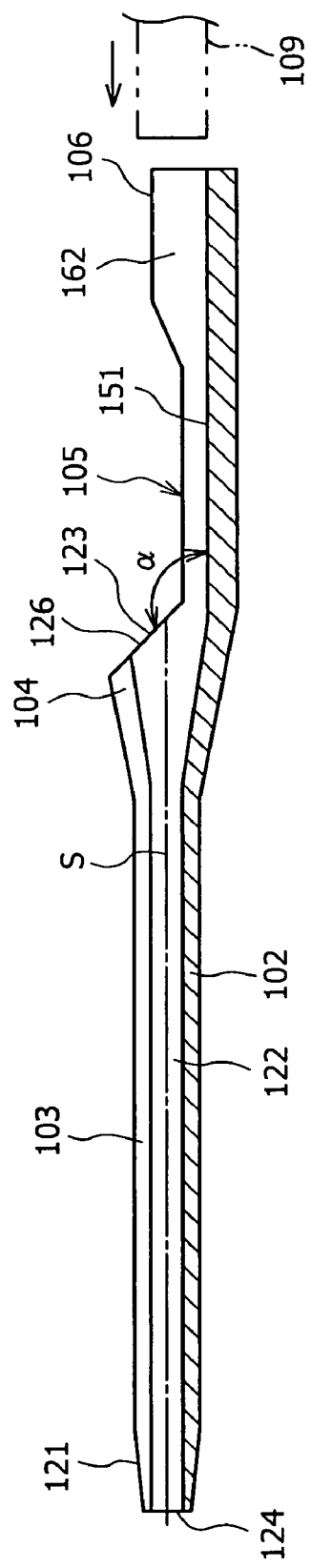
FIG. 7 is a longitudinal sectional view of the guidewire inserter shown in FIG. 6.
Figure 8:
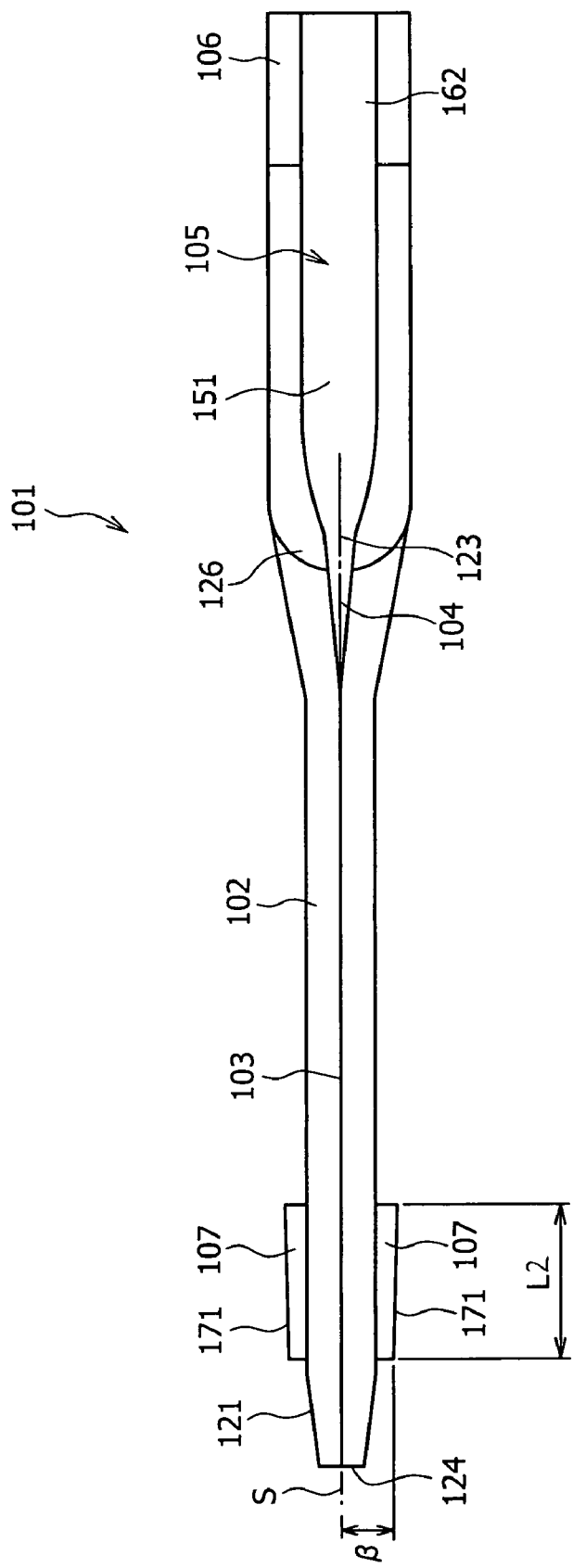
FIG. 8 is a plan view of the guidewire inserter shown in FIG. 6.
Figure 9:
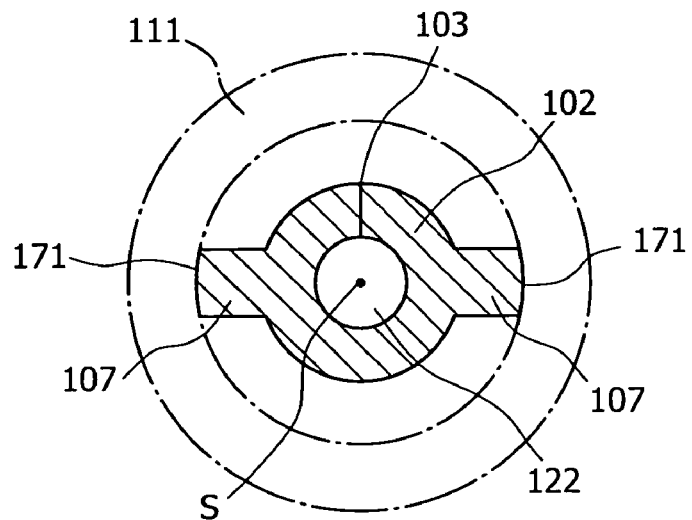
FIG. 9 is a sectional view taken along the line A-A in FIG. 6.
Figure 10:
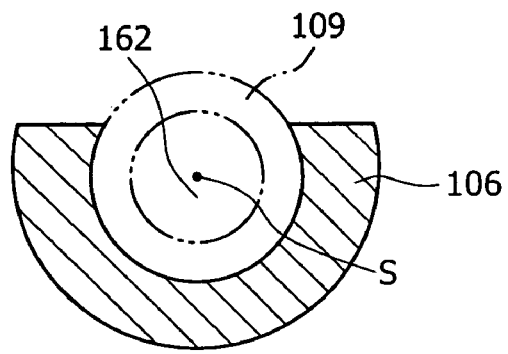
FIG. 10 is a sectional view taken along the line B-B in FIG. 6.
Figure 11:
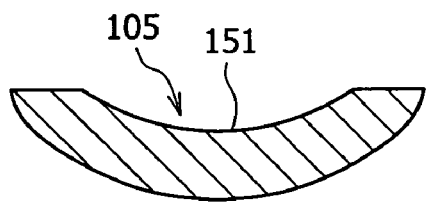
FIG. 11 is a sectional view taken along the line C-C in FIG. 6.
Figure 12:
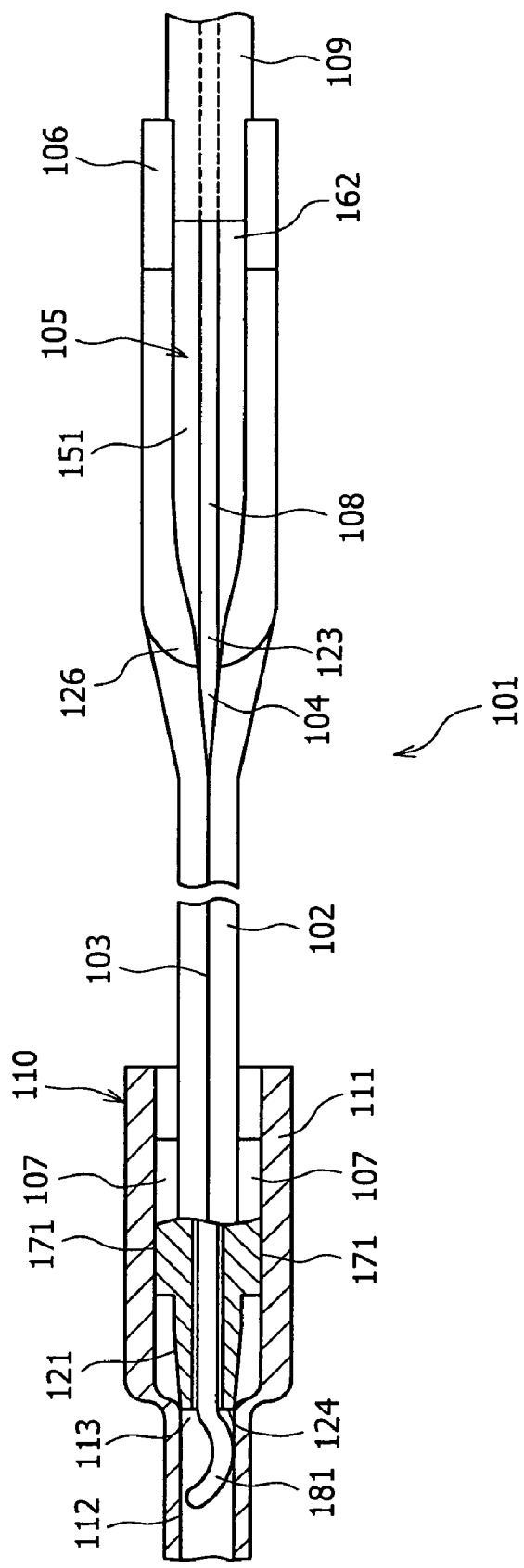
FIG. 12 is a diagram illustrating the guidewire inserter (shown in FIG. 6) connected to a tube.

FIG. 6 is a side view showing the device for introduction of a long item according to the second embodiment of the present invention. The device is used as a guidewire inserter. FIGS. 7 and 8 are respectively a longitudinal sectional view and a plan view of the guidewire inserter shown in FIG. 6. FIG. 9 is a sectional view taken along the line A-A in FIG. 6. FIG. 10 is a sectional view taken along the line B-B in FIG. 6. FIG. 11 is a sectional view taken along the line C-C in FIG. 6. FIG. 12 is a diagram illustrating the guidewire inserter (shown in FIG. 6) connected to a tube.

As shown in FIGS. 6 to 12, the guidewire inserter 101 is a tubular member 102 having a bore 122 (guidewire passage) inside that permits the guidewire 108, which is a medical long item, (described later) to pass through.

The tubular member 102 includes two parts: a cylindrical part (near the proximal end) having an approximately constant outside diameter, and a tapered part 121 having a decreasing outside diameter in going to the distal end. In this embodiment, the tapered part 121 is formed at the distal end of the tubular member 102. The tapered part 121 facilitates easy and smooth insertion of the guidewire inserter 101 into the tube 110 (mentioned later).

Incidentally, the tapered part 121 may be uniformly or stepwise tapered over its total length. Two or more tapered parts may be formed. In this embodiment, the tapered part is formed also near the inlet 123 at the proximal end of the tubular member 102.

The distal end (or the tapered part 121) of the tubular member 102 is inserted into and connected to the tube 110, such as a puncture needle, a catheter, a hub of a catheter, a Y-connector, or a sheath (not shown). It also straightens the curved tip 181 of the guidewire 108. The tapered distal end of the tubular member 102 facilitates insertion into and connection to the tube 110.

The bore 122 of the tubular member 102 has a roughly circular cross section. The distal end of the bore 122 opens at the distal end of the tubular member 102, and the proximal end of the bore 122 opens at the open part 105 (mentioned later). The proximal end opening of the bore 122 constitutes the inlet 123 for the guidewire 108, and the distal end opening of the bore 122 constitutes the outlet 124 for the guidewire 108. The shape of the inlet 123 and outlet 124 may be circle or any shape other than circle such as ellipse and polygon.

The bore 122 does not necessarily have a constant inside diameter over its total length. The illustrated bore 122 changes in inside diameter such that the inside diameter gradually increases near the proximal end in going toward the proximal end. This structure facilitates easy insertion of the guidewire 108 into the bore 122 through the inlet 123.

The inside diameter of the bore 122 should be large enough for the guidewire 108 to pass through. To be concrete, it should preferably be about 0.4 to 1.5 mm, more preferably about 0.9 to 1.3 mm.

The inside diameter (the minimum inside diameter) of the distal end of the bore 122 should preferably be slightly larger than the outside diameter of the guidewire 108, so that a clearance is left between the inside of the bore 122 and the outside of the guidewire 108. This structure helps straighten adequately the curved tip of the guidewire 108.

The tubular member 102 may be made of a stiff but somewhat resilient material, such as polyolefin (polyethylene and polypropylene), polyamide, polycarbonate, polyester (polyethylene terephthalate and polybutylene terephthalate), polyurethane, SEBS resin, fluorocarbon resin, and thermoplastic elastomer (polyolefin elastomer, polyamide elastomer, polyester elastomer, and polyurethane elastomer). They may be used alone or in combination with one another in the form of polymer alloy or laminated composite material.

The tubular member 102 has a slit 103 formed over its total length. The slit 103 penetrates the wall of the tubular member 102. The slit 103 is straight in its plan view (FIG. 8).

The slit 103 facilitates insertion of the guidewire 108 because it opens when the guidewire 108 is inserted into the bore 122 of the tubular member 102.

As shown in FIG. 9, the slit 103 has a straight cross section. In other words, it should tightly close over the entire distance from the bore 122 of the tubular member 102 to the outside of the tubular member 102. Alternatively, the slit 103 may have a Y- or V-shaped cross section, in which case it closes only at the bore side.

The slit 103 prevents the guidewire 108 from escaping from the bore 122 unexpectedly after the guidewire 108 has been inserted into the bore 122, because it tightly closes at least partly across the thickness of the wall.

As shown in FIG. 8, the slit 103 is formed such that its width gradually expands toward the proximal end, thereby constituting an aperture 104. The aperture 104 takes on a V-shape in its plan view. The end of the aperture 104 (where the aperture has the maximum width) communicates with the open space of the open part 105.

The aperture 104 facilitates insertion of the guidewire 108 into the bore 122, because it functions as a starting point for insertion. In other words, one who wants to insert the guidewire 108 into the inserter may insert the guidewire 108 into the aperture 104 and then push it into the bore 122. As the guidewire 108 is pushed into the bore 122, the slit 103 opens such that opening gradually moves to the distal end.

The aperture 104 is not specifically restricted in its length in the longitudinal direction (or the longitudinal direction of the tubular member 102); however, it should be about 5 to 100 mm long, preferably about 15 to 50 mm long.

The guidewire inserter 101 has at its proximal end a connector 106 for connection to the holder tube 109 that accommodates the guidewire 108.

The connector 106 has a C-shaped cross-section (resembling a partly cut circle), as shown in FIG. 10. The space 162 inside the connector 106 receives the guidewire 108. The holder tube 109 is connected to the connector 106 such that its distal end fits into the space 162 inside the connector 106 (as shown in FIGS. 7 and 10). The guidewire 108 being fed from the holder tube 109 enters the space 162 inside the connector 106.

The inside diameter of the connector 106 should be slightly smaller than the outside diameter of the holder tube 109, so that the space 162 slightly expands when the holder tube 109 is connected by fitting to the connector 106. This constitution ensures the holder tube 109 to firmly fit and connect to the connector 106.

The space 162 inside the connector 106 is coaxial with the bore 122 of the tubular member 102 (with its central axis being indicated by S) as shown in FIG. 7. This constitution permits the guidewire 108 to smoothly pass through the space 162 inside the connector 106, the opening 105, and the inlet 123, and to enter the bore 122 of the tubular member 102.

The shape of the connector 106 is not limited to the illustrated one; it may have any shape and structure so long as it permits connection to the holder tube 109.

Between the inlet 123 of the tubular member 102 and the connector 106 is an open part 105 at which the bore 122 of the tubular member 102 opens. This open part 105 functions as the guidewire holder that holds the guidewire 108.

As shown in FIG. 11, the open part 105 is a curved plate. However, it may also take on any shape, such as flat plate or rod.

As shown in FIG. 11, the internal surface 151 of the open part 105 should preferably be a concavely curved surface. However, it may also be a flat surface. It permits the guidewire 108 to be slid distal or proximal thereon as the guidewire 108 placed thereon is moved under pressure by a finger.

The internal surface 151 may have a surface treatment that reduces frictional resistance against the guidewire 108. In this way it is possible to feed or retract the guidewire 108 smoothly while straightening the curved tip 181. This object may be achieved by forming minute surface irregularities (emboss) or grooves (particularly those perpendicular to the longitudinal direction) on the internal surface 151 or by coating the internal surface 151 with polytetrafluoroethylene or the like that has a low coefficient of friction.

The inlet 123 of the tubular member 102 is surrounded by a slope 126 with a prescribed angle with respect to the central axis S (or the internal surface 151) of the tubular member 102. The angle $\alpha$ between the slope 126 and the internal surface 151 should preferably be about 60 to 170°, more preferably about 80 to 135°, as shown in FIG. 7. This constitution permits the guidewire 108 to be moved distal more smoothly.

As shown in FIGS. 6, 8, and 9, the distal end of the tubular member 102 has on its outer surface a pair of protruded rims 107, which project in the mutually opposite directions with respect to the central axis S of the tubular member 102. The protruded rims 107 extend in the longitudinal direction of the tubular member 102 and project symmetrically with respect to the plane containing the slit 103 (the vertical direction in FIG. 9). In other words, the two protruded rims 107 are formed at intervals of 180° in the circumferential direction of the tubular member 102.

The protruded rims 107 are formed such that they come into contact with and fit to the inner surface of the hub 111 when the distal end of the tubular member 102 is inserted into the hub 111 of the tube 110. This constitution permits stable connection between the tubular member 102 and the tube 110. For adequate connection, the protruded rims 107 should meet the following requirements.

The protruded rims 107 should have an outermost surface 171 sloped at a prescribed angle with respect to the central axis S of the tubular member 102, as shown in FIG. 8. The outermost surface 171 should be sloped such that the distal end approaches the central axis S of the tubular member 102. The protruded rims 107 having the sloped outermost surface 171 ensures stable fitting to the bore of the hub 111, because the hub 111 at the proximal end of the tube 110 is usually tapered toward the distal end as shown in FIG. 12.

The angle $\beta$ (shown in FIG. 8) between the central axis S of the tubular member 102 and the outermost surface (or sloped surface) 171 should be substantially or approximately equal to the taper angle of the tapered bore of the hub 111 into which the tubular member 102 is fitted. It should preferably be about 0.5 to 45°, more preferably about 0.8 to 10°, and most desirably 1.6 to 1.8°. This angle conforms to the ISO 594/1 Luer taper standard.

The outermost surface 171 of the protruded rims 107 has an arcuate convex cross section as shown in FIG. 9. This constitution contributes to stable fitting to the bore of the hub 111, which has usually a circular cross section. The convex outermost surface 171 should preferably have a radius of curvature of about one half the inside diameter of the hub 111.

The protruded rims 107 determine the depth of insertion into the tube 110. They also align the tubular member 102 with the tube 110, as explained in the following.

As shown in FIG. 12, the tube 110 includes the hub 111 (which has a tapered bore) and the catheter (or puncture needle) 112 (which is connected to the distal end of the hub 111). The protruded rims 107, with their outermost surfaces 171 formed properly apart, permit the distal end of the tubular member 102 to stop at an adequate position in the hub 111 at the time of insertion into the hub 111. Thus, when the tubular member 102 is fit into the hub 111, its distal end is accurately positioned. For example, as shown in FIG. 12, the outlet 124 at the distal end of the tubular member 102 can be made to approximately coincide with the position of the opening (shaft inlet) 113 at the proximal end of the catheter 112. Positioning in this manner permits the distal end of the guidewire 108 fed from the inlet 124 to be inserted into the catheter 112 smoothly and certainly.

The outermost surfaces 171 of the protruded rims 107 are equally away from the central axis S, so that the central axis of the hub 111 approximately coincides with the central axis S of the tubular member 102 at the time of insertion into the hub 111.

Thus, when the tubular member 102 is inserted into the hub 111, the center of the outlet 124 at the distal end of the tubular member 102 approximately coincides with the opening (shaft entrance) 113 at the proximal end of the catheter 112. As the result, the distal end of the guidewire 108, which has been fed from the outlet 124, is inserted into the catheter 112 smoothly and certainly.

The protruded rims 107 extend in the longitudinal direction of the tubular member 102; however, their length L2 (shown in FIG. 8) is not specifically restricted. It should be about 2 to 35%, preferably about 5 to 20%, of the total length of the guidewire inserter 101. An excessively short length L2 would lead to an instable connection to the tube 110 (hub 111), and an excessively long length L2 would make operation difficult.

As shown in FIG. 9, which is a sectional view of the tubular member 102, the angle between the two protruded rims 107 and the slit 103 is approximately 90° in the circumferential direction. This constitution helps the slit 103 to open easily and hence facilitates insertion of the guidewire 108 into the bore 122 through the slit 103.

Incidentally, the protruded rims 107 are not limited in shape to that illustrated above, but they may take on any shape. Moreover, the protruded rims 107 are not limited in number and arrangement to those shown in the drawings. However, it is desirable that they be formed at equal intervals (for example, 120° or 90°) in the circumferential direction of the tubular member 102.

The open part 105, the connector 106, and the protruded rims 107 may be made of any of polyolefin (polyethylene and polypropylene), polyamide, polycarbonate, polyester (polyethylene terephthalate and polybutylene terephthalate), polyurethane, SEBS resin, fluorocarbon resin, and thermoplastic elastomer (polyolefin elastomer, polyamide elastomer, polyester elastomer, and polyurethane elastomer). They may be used alone or in combination with one another in the form of polymer alloy or laminated composite material.

The tubular member 102, the open part 105, the connector 106, and the protruded rims 107 should preferably be formed integrally from the same material; however, they may also be formed from different materials differing in color or may be formed separately and then assembled by adhesion or fusion bonding.

Third Embodiment

Figure 13:
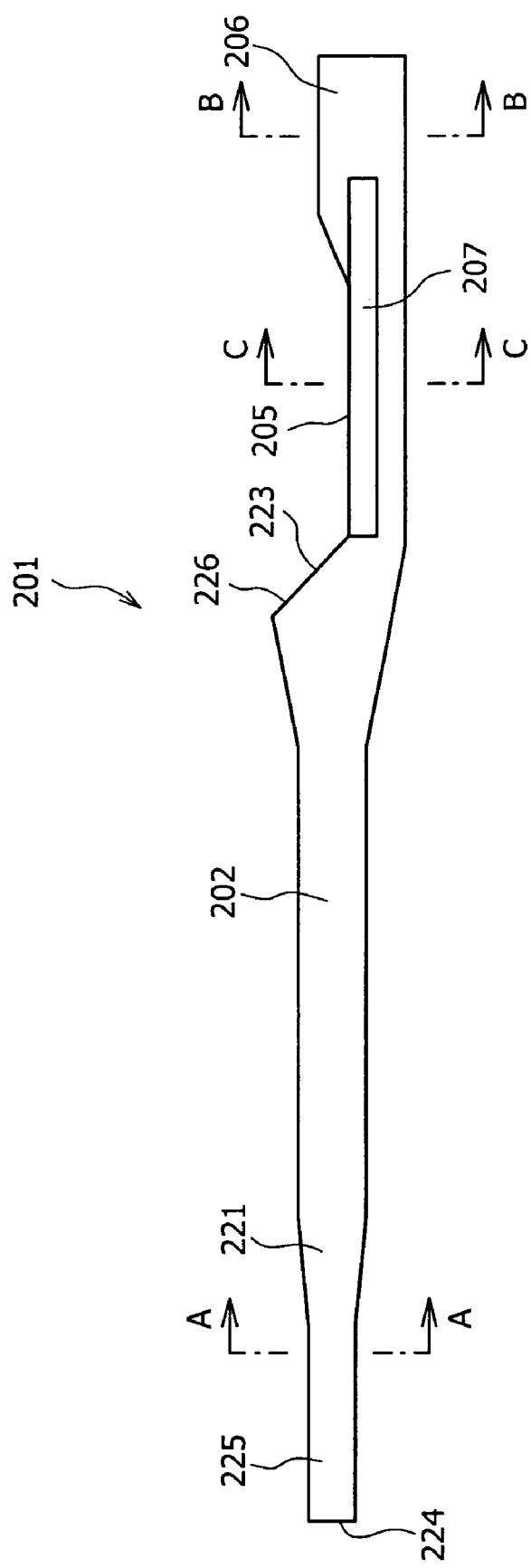
FIG. 13 is a side view showing the device for introduction of a long item according to the third embodiment of the present invention, with the device being used as a guidewire inserter.
Figure 14:
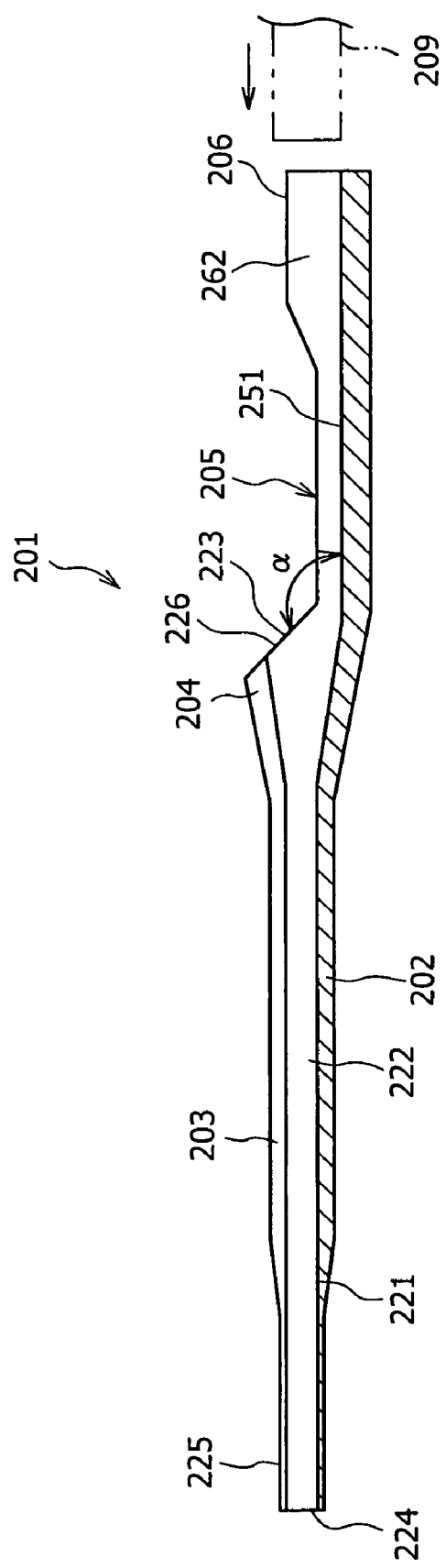
FIG. 14 is a longitudinal sectional view of the guidewire inserter shown in FIG. 13.
Figure 15:
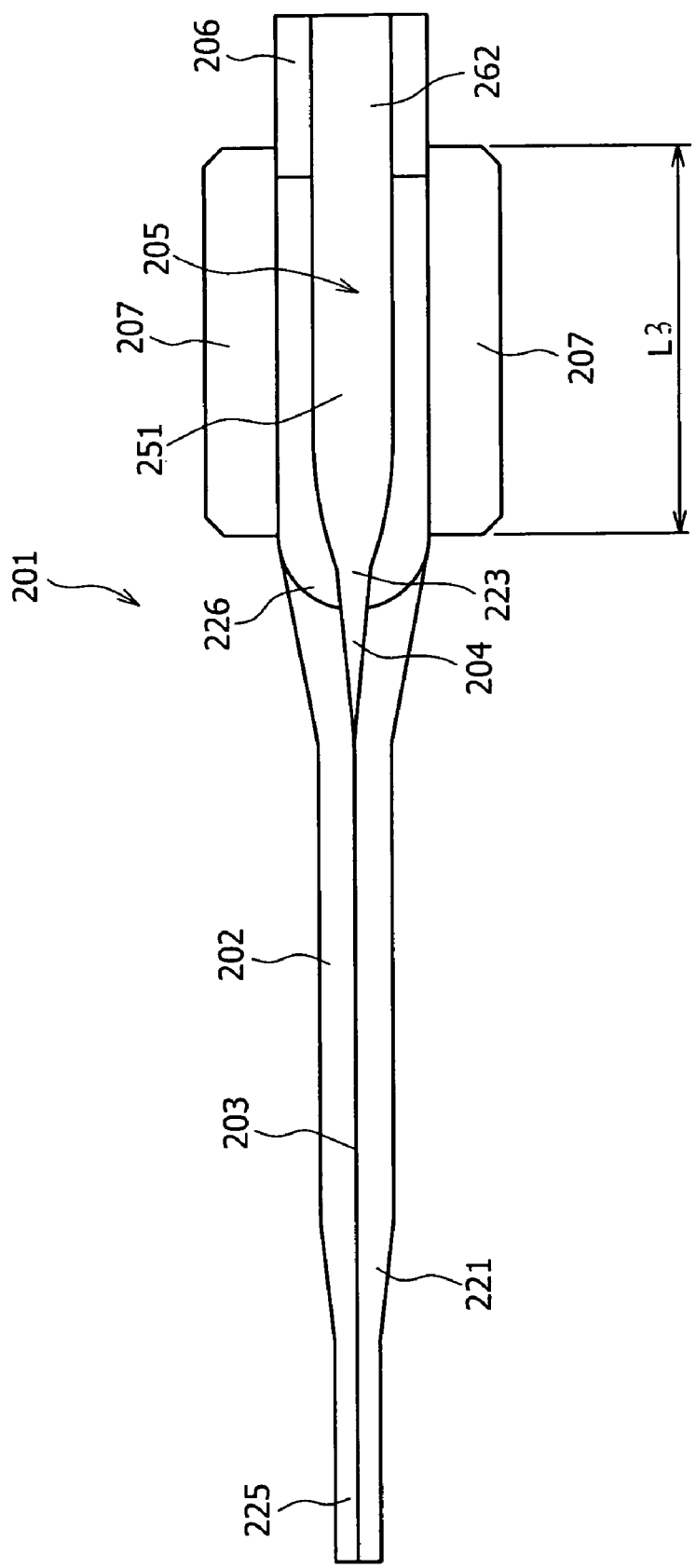
FIG. 15 is a plan view of the guidewire inserter shown in FIG. 13.
Figure 16:
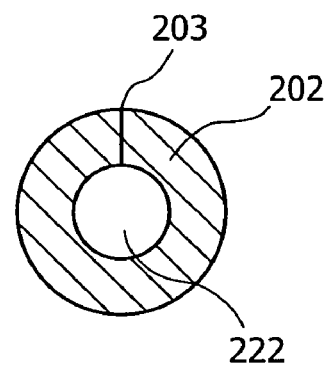
FIG. 16 is a sectional view taken along the line A-A in FIG. 13.
Figure 17:
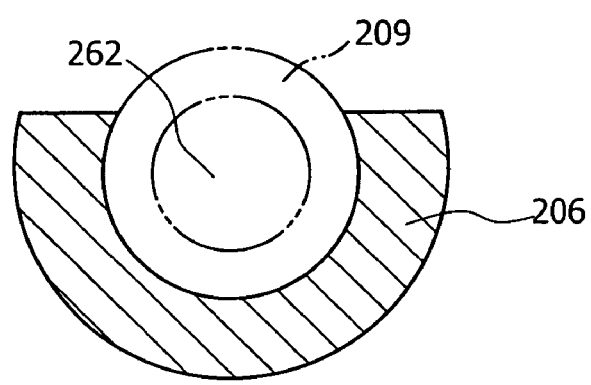
FIG. 17 is a sectional view taken along the line B-B in FIG. 13.
Figure 18:
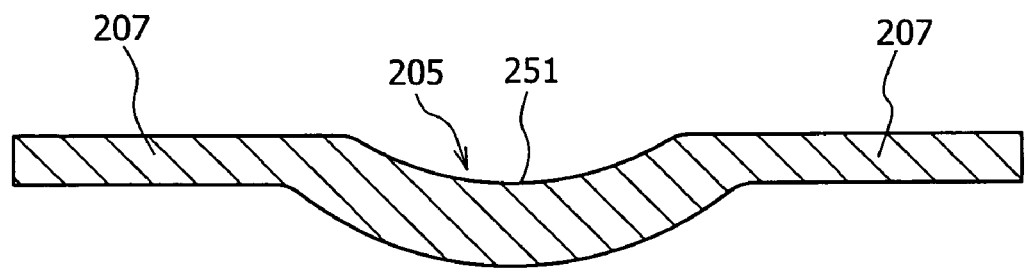
FIG. 18 is a sectional view taken along the line C-C in FIG. 13.

FIG. 13 is a side view showing the device for introduction of a long item according to the third embodiment of the present invention. The device is used as a guidewire inserter. FIGS. 14 and 15 are respectively a longitudinal sectional view and a plan view of the guidewire inserter shown in FIG. 13. FIG. 16 is a sectional view taken along the line A-A in FIG. 13. FIG. 17 is a sectional view taken along the line B-B in FIG. 13. FIG. 18 is a sectional view taken along the line C-C in FIG. 13.

As shown in FIGS. 13 to 18, the guidewire inserter 201 is a tubular member 202 having a bore 222 (guidewire passage) inside that permits the guidewire, which is a medical long item, to pass through.

The tubular member 202 includes two parts: a cylindrical part (near the proximal end) having an approximately constant outside diameter, and a tapered part 221 having a decreasing outside diameter in going to the distal end. The tapered part 221 facilitates easy and smooth insertion of the guidewire inserter 201 into the sheath or the like (mentioned later).

Incidentally, the tapered part 221 may be uniformly or stepwise tapered over its total length. Two or more tapered parts may be formed.

The distal end 225 of the tubular member 202 is smaller in outside diameter than other parts. It may be tapered toward the distal end. It is inserted into and connected to a puncture needle, catheter, a hub of a catheter, Y-connector, or a sheath (not shown). It also straightens the curved tip of the guidewire. Being smaller than other parts, particularly being tapered distal, it facilitates insertion into and connection to the sheath or the like.

Where it is necessary to connect the tubular member 202 to a device (like Y-connector) in which the space therein branches away, the distal end 225 of the tubular member 102 may be provided with a thin tubular member having a tapered end (which is prepared separately). Such an additional tubular member permits the guidewire (with its curved tip straightened) to be inserted into a Y-connector, while preventing the curved tip from entering the branch in the Y-connector.

The bore 222 of the tubular member 202 has an approximately circular cross section. The distal end of the bore 222 opens at the distal end of the tubular member 202, and the proximal end of the bore 222 opens at the open part 205 (mentioned later). The proximal end opening of the bore 222 constitutes the inlet 223 for the guidewire, and the distal end opening of the bore 222 constitutes the outlet 224 for the guidewire. The shape of the inlet 223 and outlet 224 may be circle or any shape other than circle such as ellipse and polygon.

The bore 222 does not necessarily have a constant inside diameter over its total length. The illustrated bore 222 changes in inside diameter such that the inside diameter gradually increases near the proximal end in going toward the proximal end. This structure facilitates easy insertion of the guidewire into the bore 222 through the inlet 223.

The inside diameter of the bore 222 should be large enough for the guidewire to pass through. To be concrete, it should preferably be about 0.4 to 1.5 mm, more preferably about 0.9 to 1.3 mm.

The inside diameter (the minimum inside diameter) of the distal end of the bore 222 should preferably be slightly larger than the outside diameter of the guidewire, so that a clearance is left between the inside of the bore 222 and the outside of the guidewire. This structure helps straighten adequately the curved tip of the guidewire.

The tubular member 202 may be made of a stiff but somewhat resilient material, such as polyolefin (polyethylene and polypropylene), polyamide, polycarbonate, polyester (polyethylene terephthalate and polybutylene terephthalate), polyurethane, SEBS resin, fluorocarbon resin, and thermoplastic elastomer (polyolefin elastomer, polyamide elastomer, polyester elastomer, and polyurethane elastomer). They may be used alone or in combination with one another in the form of polymer alloy or laminated composite material.

The tubular member 202 has a slit 203 formed over its total length. The slit 203 cuts across the wall of the tubular member 202. The slit 203 is straight in its plan view (FIG. 15).

The slit 203 facilitates insertion of the guidewire because it opens when the guidewire is inserted into the bore 222 of the tubular member 202.

As shown in FIG. 16, the slit 203 has a straight cross section. In other words, it should tightly close over the entire distance from the bore 222 of the tubular member 202 to the outside of the tubular member 202. Alternatively, the slit 203 may have a Y- or V-shaped cross section, in which case it closes only at the bore side.

The slit 203 prevents the guidewire from escaping from the bore 222 unexpectedly after the guidewire has been inserted into the bore 222, because it tightly closes at least partly across the thickness of the wall.

As shown in FIG. 15, the slit 203 is formed such that its width gradually expands toward the proximal end, thereby constituting an aperture 204. The aperture 204 takes on a V-shape in its plan view. The end of the aperture 204 (where the aperture has the maximum width) communicates with the open space of the open part 205.

The aperture 204 facilitates insertion of the guidewire into the bore 222, because it functions as a starting point for insertion. In other words, one who wants to insert the guidewire into the inserter may insert the guidewire into the aperture 204 and then push it into the bore 222. As the guidewire is pushed into the bore 222, the slit 203 opens such that opening gradually moves to the distal end.

The aperture 204 is not specifically restricted in its length in the longitudinal direction (or the longitudinal direction of the tubular member 202); however, it should be about 5 to 100 mm long, preferably about 15 to 50 mm long.

The guidewire inserter 201 has at its proximal end a connector 206 for connection to the holder tube 209 that accommodates the guidewire.

The connector 206 has a C-shaped cross-section (resembling a partly cut circle), as shown in FIG. 17. The space 262 inside the connector 206 receives the guidewire. The holder tube 209 is connected to the connector 206 such that its distal end fits into the space 262 inside the connector 206 (as shown in FIGS. 14 and 17). The guidewire being fed from the holder tube 209 enters the space 262 inside the connector 206.

The inside diameter of the connector 206 should be slightly smaller than the outside diameter of the holder tube 209, so that the space 262 slightly expands when the holder tube 209 is connected by fitting to the connector 206. This constitution ensures the holder tube 209 to firmly fit and connect to the connector 206.

The space 262 inside the connector 206 is coaxial with the bore 222 of the tubular member 202. This constitution permits the guidewire to smoothly pass through the space 262 inside the connector 206, the opening 205, and the inlet 223, and to enter the bore 222 of the tubular member 202.

The shape of the connector 206 is not limited to the illustrated one; it may have any shape and structure so long as it permits connection to the holder tube 209.

Between the inlet 223 of the tubular member 202 and the connector 206 is an open part 205 at which the bore 222 of the tubular member 202 opens. This open part 205 functions as the guidewire holder that holds the guidewire. As shown in FIG. 18, the internal surface 251 of the open part 205 should preferably be a concavely curved surface or a flat surface. It permits the guidewire to be slid distal or proximal thereon as the guidewire placed thereon is moved under pressure by a finger.

The internal surface 251 may have a surface treatment that reduces frictional resistance against the guidewire. In this way it is possible to feed or retract the guidewire smoothly. This object may be achieved by forming minute surface irregularities (emboss) or grooves (particularly those perpendicular to the longitudinal direction) on the internal surface 251 or by coating the internal surface 251 with polytetrafluoroethylene or the like that has a low coefficient of friction.

The inlet 223 of the tubular member 202 is surrounded by a slope 226 with a prescribed angle with respect to the central axis (or the internal surface 251) of the tubular member 202. The angle α between the slope 226 and the internal surface 251 should preferably be about 60 to 170°, more preferably about 80 to 135°, as shown in FIG. 14. This constitution permits the guidewire to be moved distal more smoothly.

As shown in FIGS. 15 and 18, the open part 205 has on its both sides a pair of wing-like protruded pieces 207, which project in the mutually opposite direction from the central axis of the guidewire inserter 201.

The flat protruded pieces 207 help the operator to hold both the guidewire and the guidewire inserter 201 simultaneously with one hand.

The protruded pieces 207 may be curved so that they are fit well with the operator's fingers. Thus, they help the operator to hold more easily both the guidewire and the guidewire inserter 201 simultaneously with one hand.

The protruded pieces 207 may be composed of a curved part and a flat part, so that the flat part helps the operator to hold both the guidewire and the guidewire inserter 201 simultaneously with one hand if the curved part does not fit well with the operator's fingers.

The protruded pieces 207 should have a length L3 (in the longitudinal direction of the tubular member 202), which is about 10 to 50%, preferably about 20 to 40%, of the total length of the guidewire inserter 201. This length is suitable for easy holding and good operation.

The protruded pieces 207 and the open part 205 should preferably be formed in such a way that they partly (preferably more than half, more preferably entirely) overlap with each other in the longitudinal direction. This constitution permits the guidewire to be moved distal and proximal (to straighten the curved tip) more easily.

The open part 205, the connector 206, and the protruded prices 207 may be made of any of polyolefin (polyethylene and polypropylene), polyamide, polycarbonate, polyester (polyethylene terephthalate and polybutylene terephthalate), polyurethane, SEBS resin, fluorocarbon resin, and thermoplastic elastomer (polyolefin elastomer, polyamide elastomer, polyester elastomer, and polyurethane elastomer). They may be used alone or in combination with one another in the form of polymer alloy or laminated composite material.

The tubular member 202, the open part 205, the connector 206, and the protruded pieces 207 should preferably be formed integrally from the same material; however, they may also be formed from different materials differing in color or may be formed separately and then assembled by adhesion or fusion bonding.

Fourth Embodiment

Figure 19:
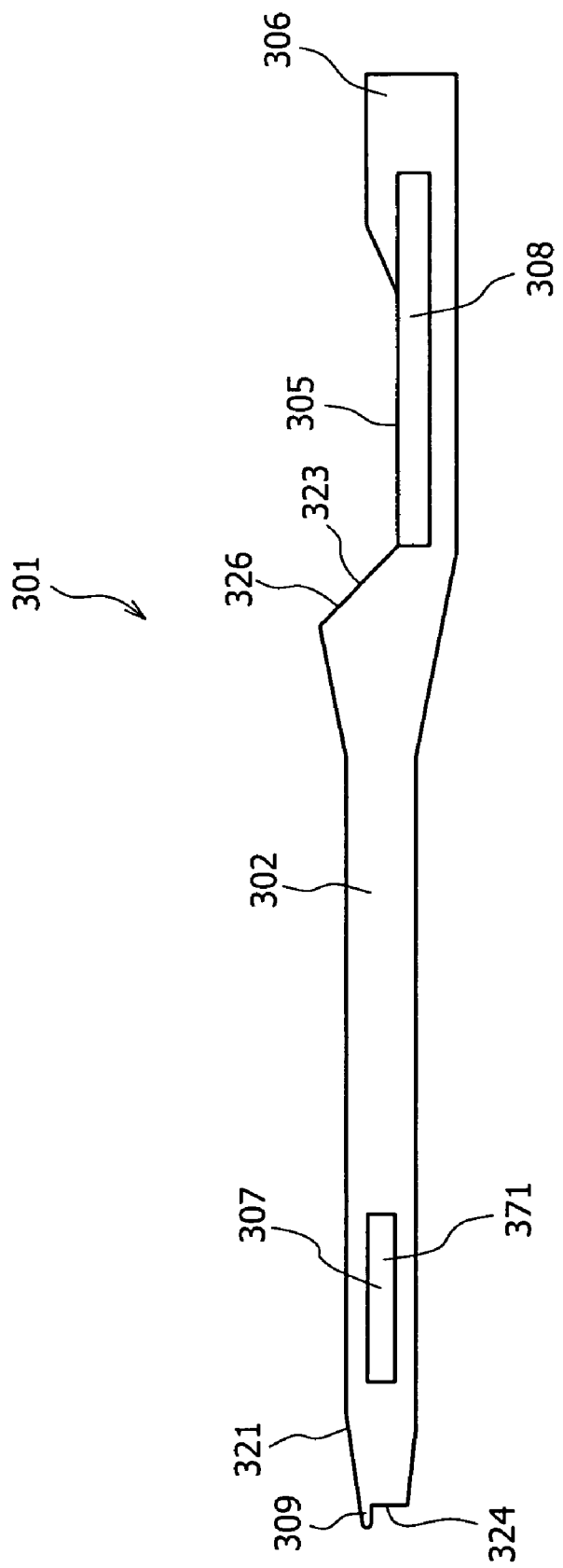
FIG. 19 is a side view showing the device for introduction of a long item according to the fourth embodiment of the present invention, with the device being used as a guidewire inserter.

FIG. 19 is a side view showing the device for introduction of a long item according to the fourth embodiment of the present invention. The device is used as a guidewire inserter.

Figure 20:
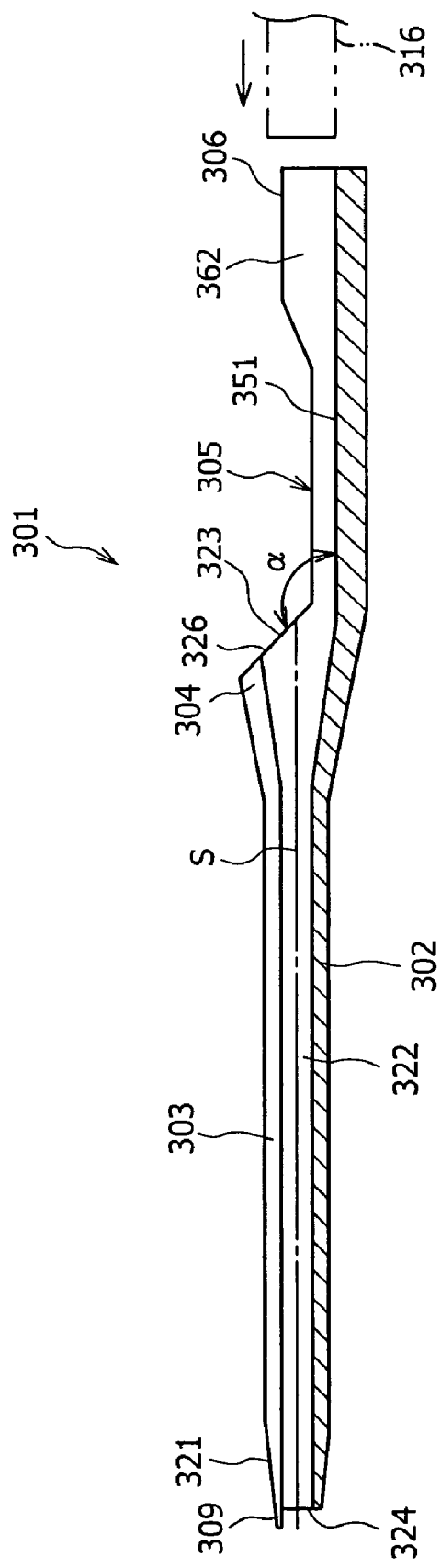
FIG. 20 is a longitudinal sectional view of the guidewire inserter shown in FIG. 19.
Figure 21:
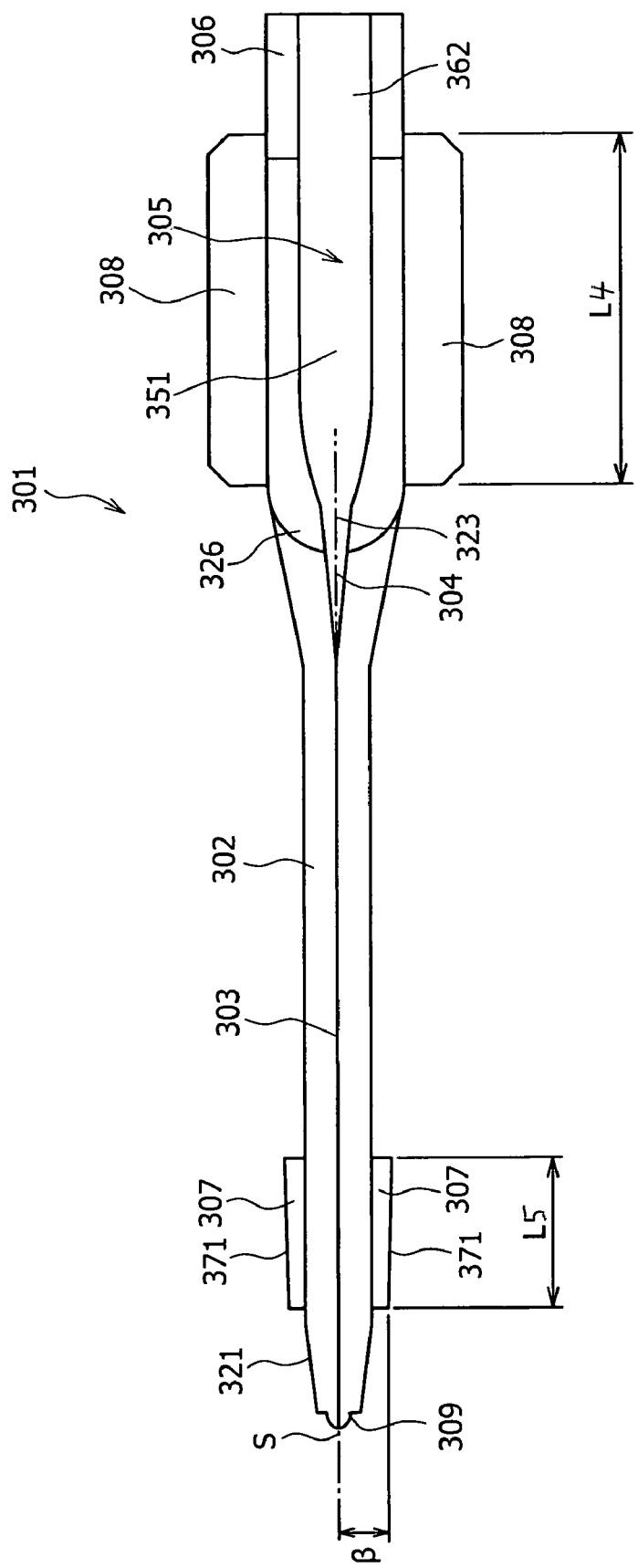
FIG. 21 is a plan view of the guidewire inserter shown in FIG. 19.

FIGS. 20 and 21 are respectively a longitudinal sectional view and a plan view of the guidewire inserter shown in FIG. 19. FIGS. 22 to 27 are views illustrating how to use the guidewire inserter shown in FIGS. 19 to 21.

As shown in FIGS. 19 to 21, the guidewire inserter 301 is a tubular member 302 having a bore 322 (guidewire passage) inside that permits the guidewire 314, which is a medical long item, to pass through.

The tubular member 302 includes two parts: a cylindrical part (near the proximal end) having an approximately constant outside diameter, and a tapered part 321 having a decreasing outside diameter in going to the distal end. In this embodiment, the tapered part 321 is formed at the distal end of the tubular member 302. The tapered part 321 facilitates easy and smooth insertion of the guidewire inserter 301 into the tube 310 (mentioned later).

Incidentally, the tapered part 321 may be uniformly or stepwise tapered over its total length. Two or more tapered parts may be formed. In this embodiment, the tapered part 321 is formed also near the inlet 323 at the proximal end of the tubular member 302.

The distal end (or the tapered part 321) of the tubular member 302 is inserted into and connected to the tube 310, such as a puncture needle, a catheter, a hub of a catheter, a Y-connector, or a sheath (not shown). It also straightens the curved tip 315 of the guidewire 314. The tapered distal end of the tubular member 302 facilitates insertion into and connection to the tube 310.

The bore 322 of the tubular member 302 has an approximately circular cross section. The distal end of the bore 322 opens at the distal end of the tubular member 302, and the proximal end of the bore 322 opens at the open part 305 (mentioned later). The proximal end opening of the bore 322 constitutes the inlet 323 for the guidewire 314, and the distal end opening of the bore 322 constitutes the outlet 324 for the guidewire 314. The shape of the inlet 323 and outlet 324 may be circle or any shape other than circle such as ellipse and polygon.

The bore 322 does not necessarily have a constant inside diameter over its total length. The illustrated bore 322 changes in inside diameter such that the inside diameter gradually increases near the proximal end in going toward the proximal end. This structure facilitates easy insertion of the guidewire 314 into the bore 322 through the inlet 323.

The inside diameter of the bore 322 should be large enough for the guidewire 314 to pass through. To be concrete, it should preferably be about 0.4 to 1.5 mm, more preferably about 0.9 to 1.3 mm.

The inside diameter (the minimum inside diameter) of the distal end of the bore 322 should preferably be slightly larger than the outside diameter of the guidewire 314, so that a clearance is left between the inside of the bore 322 and the outside of the guidewire 314. This structure helps straighten adequately the curved tip of the guidewire 314.

The tubular member 302 may be made of a stiff but somewhat resilient material, such as polyolefin (polyethylene and polypropylene), polyamide, polycarbonate, polyester (polyethylene terephthalate and polybutylene, terephthalate), polyurethane, SEBS resin, fluorocarbon resin, and thermoplastic elastomer (polyolefin elastomer, polyamide elastomer, polyester elastomer, and polyurethane elastomer). They may be used alone or in combination with one another in the form of polymer alloy or laminated composite material.

The tubular member 302 has a slit 303 formed over its total length. The slit 303 cuts across the wall of the tubular member 302. The slit 303 is straight in its plan view (FIG. 21).

The slit 303 facilitates insertion of the guidewire 314 because it opens when the guidewire 314 is inserted into the bore 322 of the tubular member 302.

The slit 303 has a straight cross section. In other words, it should tightly close over the entire distance from the bore 322 of the tubular member 302 to the outside of the tubular member 302. Alternatively, the slit 303 may have a Y- or V-shaped cross section, in which case it closes only at the bore side.

The slit 303 prevents the guidewire 314 from escaping from the bore 322 unexpectedly after the guidewire 314 has been inserted into the bore 322, because it tightly closes at least partly across the thickness of the wall.

As shown in FIG. 21, the slit 303 is formed such that its width gradually expands toward the proximal end, thereby constituting an aperture 304. The aperture 304 takes on a V-shape in its plan view. The end of the aperture 304 (where the aperture has the maximum width) communicates with the open space of the open part 305.

The aperture 304 facilitates insertion of the guidewire 314 into the bore 322, because it functions as a starting point for insertion. In other words, one who wants to insert the guidewire 314 into the inserter may insert the guidewire 314 into the aperture 304 and then push it into the bore 322. As the guidewire 314 is pushed into the bore 322, the slit 303 opens such that opening gradually moves to the distal end.

The aperture 304 is not specifically restricted in its length in the longitudinal direction (or the longitudinal direction of the tubular member 302); however, it should be about 5 to 100 mm long, preferably about 15 to 50 mm long.

The tubular member 302 has a projection 309 at its distal end. This projection 309 is a distally projecting part of the circumferential direction of the tubular member 302. (This part is at the upper side in FIGS. 19 and 20.) This projection 309 takes on a mountain-like shape, with a vertex and slopes, in its plan view (FIG. 21). The slit 303 passes through the vertex of the mountain-like shape of the projection 309. In other words, the projection 309 is symmetrical with respect to the slit 303. The projection may also be formed such that the slit 303 passes through the slope of the mountain shape.

The projection 309 contributes to strength and prevents the curved tip 315 of the guidewire 314 from being caught by the slit 303 when the curved tip 315 is straightened at the tapered part 321. Therefore, it facilitates straightening of the curved tip 315 of the guidewire 314 and also facilitates insertion of the guidewire 314 into the puncture needle, catheter, or sheath.

The projection 309 is not specifically restricted in the projecting length in the distal direction; however, the projecting length should preferably be no shorter than 1 mm, more preferably about 1 to 3 mm.

The guidewire inserter 301 has at its proximal end a connector 306 for connection to the holder tube 316 that accommodates the guidewire 314.

The connector 306 has a C-shaped cross-section (resembling a partly cut circle). The space 362 inside the connector 306 receives the guidewire 314. The holder tube 316 is connected to the connector 306 such that its distal end fits into the space 362 inside the connector 306 (as shown in FIG. 20). The guidewire 314 being fed from the holder tuber 316 enters the space 362 inside the connector 306.

The inside diameter of the connector 306 should be slightly smaller than the outside diameter of the holder tube 316, so that the space 362 slightly expands when the holder tube 316 is connected by fitting to the connector 306. This constitution ensures the holder tube 316 to firmly fit and connect to the connector 306.

The space 362 inside the connector 306 is coaxial with the bore 322 of the tubular member 302 (with its central axis being indicated by S) as shown in FIG. 20. This constitution permits the guidewire 314 to smoothly pass through the space 362 inside the connector 306, the opening 305, and the inlet 323, and to enter the bore 322 of the tubular member 302.

The shape of the connector 306 is not limited to the illustrated one; it may have any shape and structure so long as it permits connection to the holder tube 316.

Between the inlet 323 of the tubular member 302 and the connector 306 is an open part 305 at which the bore 322 of the tubular member 302 opens. This open part 305 functions as the guidewire holder that holds the guidewire 314.

The open part 305 is a curved plate. However, it may also take on any shape, such as flat plate or rod.

The internal surface 351 of the open part 305 should preferably be a concavely curved surface. However, it may also be a flat surface. It permits the guidewire 314 to be slid distal or proximal thereon as the guidewire 314 placed thereon is moved under pressure by a finger.

The internal surface 351 may have a surface treatment that reduces frictional resistance against the guidewire 314. In this way it is possible to feed or retract the guidewire 314 smoothly while straightening the curved tip 315. This object may be achieved by forming minute surface irregularities (emboss) or grooves (particularly those perpendicular to the longitudinal direction) on the internal surface 351 or by coating the internal surface 351 with polytetrafluoroethylene or the like that has a low coefficient of friction.

The inlet 323 of the tubular member 302 is surrounded by a slope 326 with a prescribed angle with respect to the central axis S (or the internal surface 351) of the tubular member 302. The angle α between the slope 326 and the internal surface 351 should preferably be about 60 to 170°, more preferably about 80 to 135°, as shown in FIG. 20. This constitution permits the guidewire 314 to be moved distal more smoothly.

As shown in FIGS. 19 and 21, the open part 305 has on its both sides a pair of wing-like protruded pieces 308, which project in the mutually opposite direction from the central axis of the guidewire inserter 301.

The flat protruded pieces 308 help the operator to hold both the guidewire and the guidewire inserter 301 simultaneously with one hand.

The protruded pieces 308 may be curved so that they are fit well with the operator's fingers. Thus, they help the operator to hold more easily both the guidewire and the guidewire inserter 301 simultaneously with one hand.

The protruded pieces 308 may be composed of a curved part and a flat part, so that the flat part helps the operator to hold both the guidewire and the guidewire inserter 301 simultaneously with one hand if the curved part does not fit well with the operator's fingers.

The protruded pieces 308 should have a length L4 (in the longitudinal direction of the tubular member 302), which is about 10 to 50%, preferably about 20 to 40%, of the total length of the guidewire inserter 301. This length is suitable for easy holding and good operation.

The protruded pieces 308 and the open part 305 should preferably be formed in such a way that they partly (preferably more than half, more preferably entirely) overlap with each other in the longitudinal direction. This constitution permits the guidewire to be moved distal and proximal (to straighten the curved tip) more easily.

As shown in FIGS. 19 and 21, the distal end of the tubular member 302 has on its outer surface a pair of protruded rims 307, which project in mutually opposite directions with respect to the central axis S of the tubular member 302. The protruded rims 307 extend in the longitudinal direction of the tubular member 302 and project symmetrically with respect to the plane containing the slit 303. In other words, the two protruded rims 307 are formed at intervals of 180° in the circumferential direction of the tubular member 302.

The protruded rims 307 are formed such that they come into contact with and fit to the inner surface of the hub 311 when the distal end of the tubular member 302 is inserted into the hub 311 of the tube 310. This constitution permits stable connection between the tubular member 302 and the tube 310. For adequate connection, the protruded rims 307 should meet the following requirements.

Figure 27:
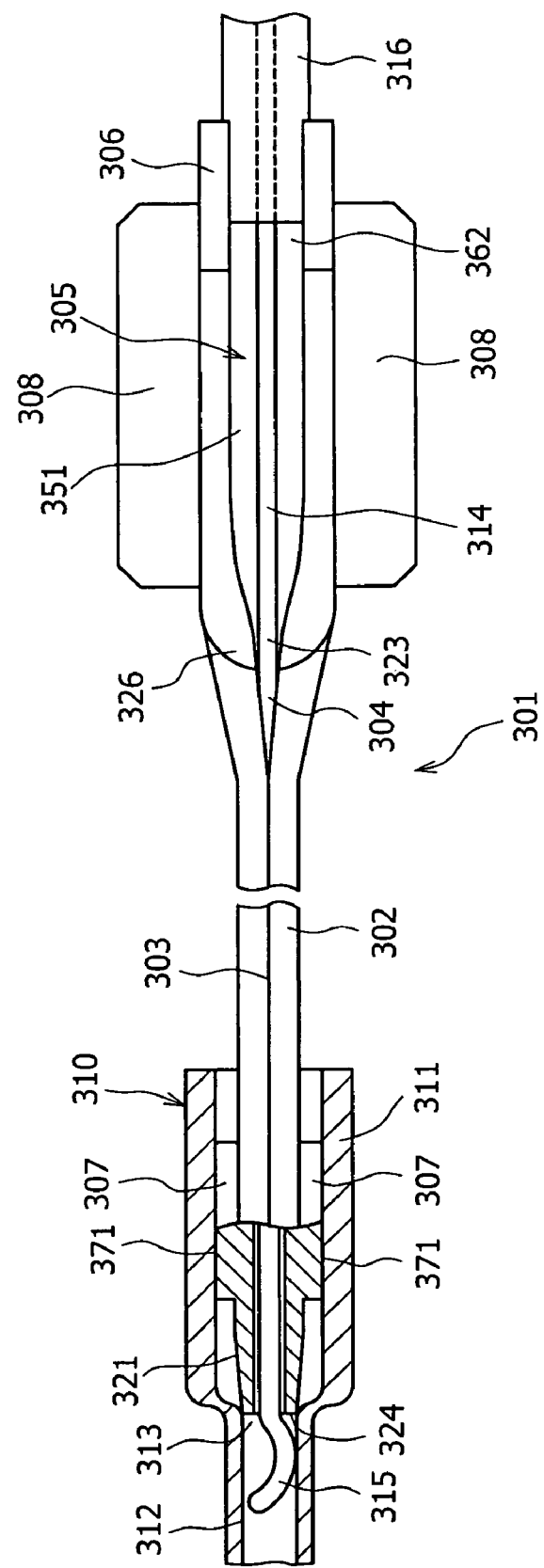
FIG. 27 is a partly sectional plan view illustrating how to use the guidewire inserter according to the present invention.

The protruded rims 307 should have an outermost surface 371, which is sloped at a prescribed angle with respect to the central axis S of the tubular member 302, as shown in FIG. 21. The outermost surface 371 should be sloped such that the distal end approaches the central axis S of the tubular member 302. The protruded rims 307 having the sloped outermost surface 371 ensures stable fitting to the bore of the hub 311, because the hub 311 at the proximal end of the tube 310 is usually tapered toward the distal end as shown in FIG. 27.

The angle β (shown in FIG. 21) between the central axis S of the tubular member 302 and the outermost surface (or sloped surface) 371 should be substantially or approximately equal to the taper angle of the tapered bore of the hub 311 into which the tubular member 302 is fitted. It should preferably be about 0.5 to 45°, more preferably about 0.8 to 10°, and most desirably 1.6 to 1.8°. This angle conforms to the ISO 594/1 Luer taper standard.

The outermost 371 surface of the protruded rims 307 has an arcuate convex cross section. This constitution contributes to stable fitting to the bore of the hub 311, which has usually a circular cross section. The convex outermost surface 371 should preferably have a radius of curvature of about one half the inside diameter of the hub 311.

The protruded rims 307 determine the depth of insertion into the tube 310. They also align the tubular member 302 with the tube 310, as explained in the following.

As shown in FIG. 27, the tube 310 includes the hub 311 (which has a tapered bore) and the catheter (or puncture needle) 312 (which is connected to the distal end of the hub 311). The protruded rims 307, with their outermost surfaces 371 formed properly apart, permit the distal end of the tubular member 302 to stop at an adequate position in the hub 311 at the time of insertion into the hub 311. Thus, when the tubular member 302 is fit into the hub 311, its distal end is accurately positioned. For example, as shown in FIG. 27, the outlet 324 at the distal end of the tubular member 302 can be made to approximately coincide with the position of the opening (shaft inlet) 313 at the proximal end of the catheter 312. Positioning in this manner permits the distal end of the guidewire 314 fed from the inlet 324 to be inserted into the catheter 312 smoothly and certainly.

The outermost surfaces 371 of the protruded rims 307 are equally away from the central axis S, so that the central axis of the hub 311 approximately coincides with the central axis S of the tubular member 302 at the time of insertion into the hub 311.

Thus, when the tubular member 302 is inserted into the hub 311, the center of the outlet 324 at the distal end of the tubular member 302 approximately coincides with the opening (shaft entrance) 313 at the proximal end of the catheter 312. As the result, the distal end of the guidewire 314, which has been fed from the outlet 324, is inserted into the catheter 312 smoothly and certainly.

The protruded rims 307 extend in the longitudinal direction of the tubular member 302; however, their length L5 (shown in FIG. 21) is not specifically restricted. It should be about 2 to 35%, preferably about 5 to 20%, of the total length of the guidewire inserter 301. An excessively short length L5 would lead to an instable connection to the tube 310 (hub 311), and an excessively long length L5 would make operation difficult.

The angle between the two protruded rims 307 and the slit 303 is approximately 90° in the circumferential direction. This constitution helps the slit 303 to open easily and hence facilitates insertion of the guidewire 314 into the bore 322 through the slit 303.

Incidentally, the protruded rims 307 are not limited in shape to that illustrated above, but they may take on any shape. Moreover, the protruded rims 307 are not limited in number and arrangement to those shown in the drawings. However, it is desirable that they be formed at equal intervals (for example, 120° or 90°) in the circumferential direction of the tubular member 302.

The open part 305, the connector 306, the protruded rims 307, and the protruded pieces 308 may be made of any of polyolefin (polyethylene and polypropylene), polyamide, polycarbonate, polyester (polyethylene terephthalate and polybutylene terephthalate), polyurethane, SEBS resin, fluorocarbon resin, and thermoplastic elastomer (polyolefin elastomer, polyamide elastomer, polyester elastomer, and polyurethane elastomer). They may be used alone or in combination with one another in the form of polymer alloy or laminated composite material.

The tubular member 302, the open part 305, the connector 306, the protruded rims 307, and the protruded pieces 308 should preferably be formed integrally from the same material. However, they may also be formed from different materials differing in color or may be formed separately and then assembled by adhesion or fusion bonding.

According to the present invention, the guidewire inserter is used in the way explained below with reference to FIGS. 22 to 27.

Figure 22:
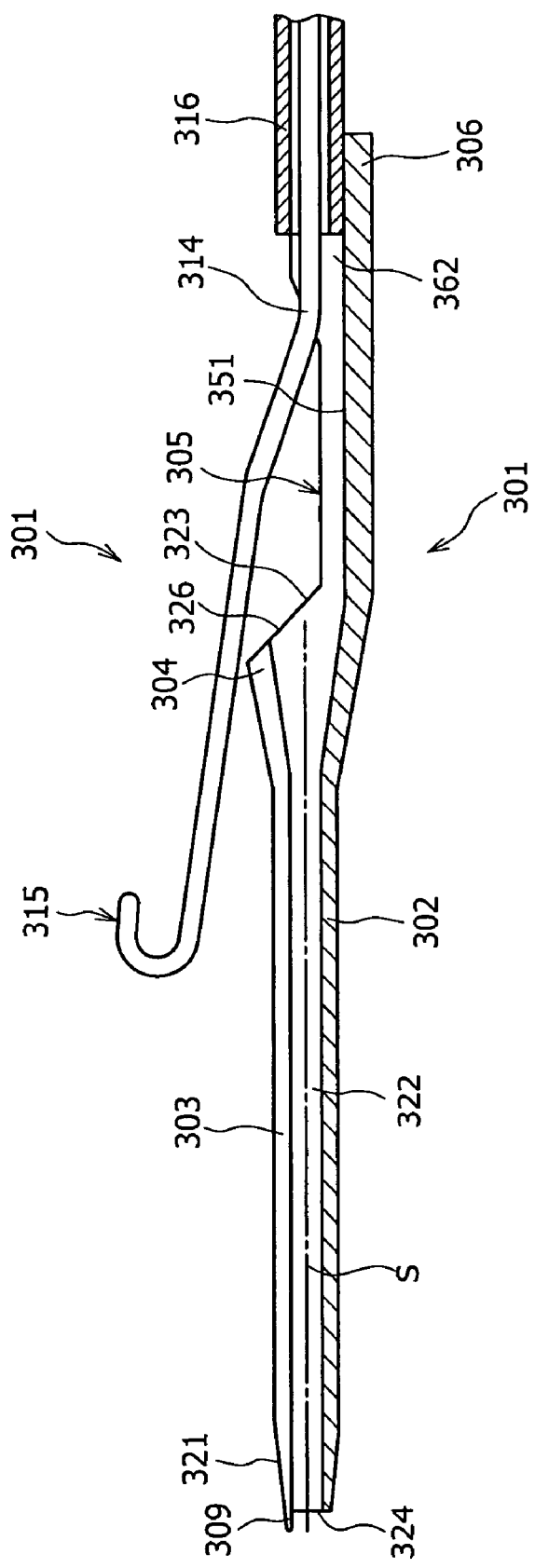
FIG. 22 is a sectional side view illustrating how to use the guidewire inserter according to the present invention.

In the first step shown in FIG. 22, the connector 306 of the guidewire inserter 301 is connected to the distal end of the holder tube 316. The guidewire 314 is fed to distal by pushing it with the finger against the internal surface 351 of the open part 305, while holding the open part 305 and the protruded pieces 308 with one hand.

Figure 23:
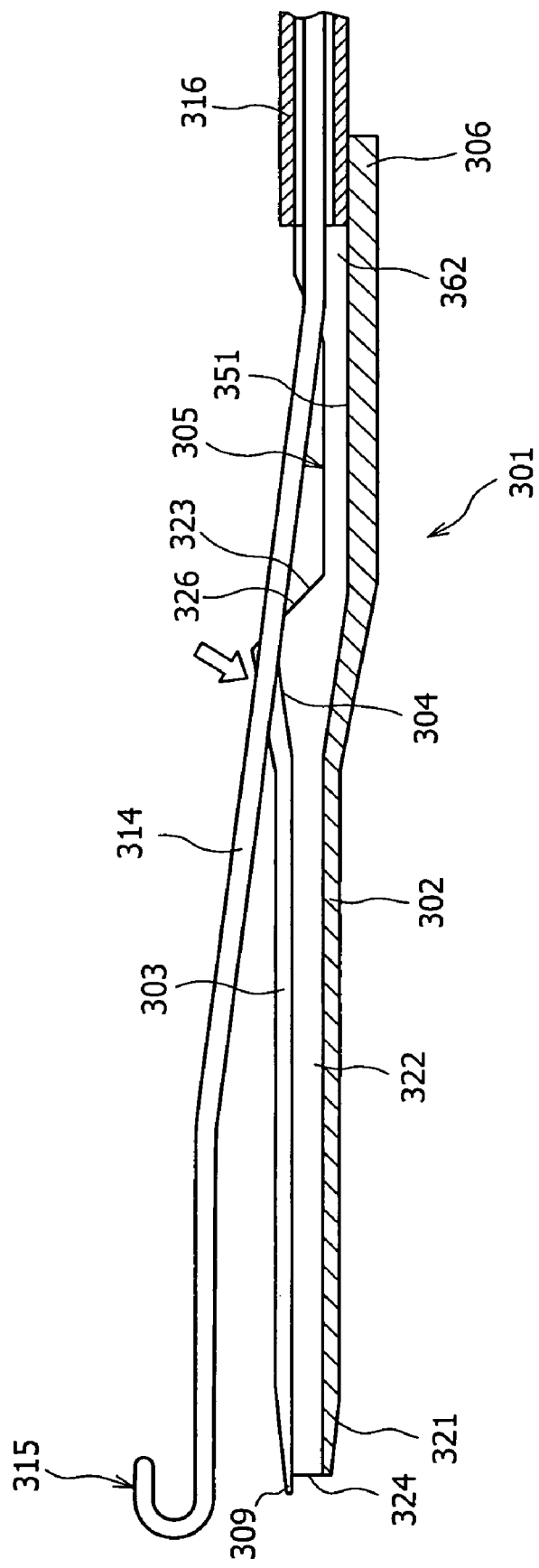
FIG. 23 is a sectional side view illustrating how to use the guidewire inserter according to the present invention.

In the next step shown in FIG. 23, the guidewire 314 is inserted into the aperture 304, while keeping the curved tip 315 of the guidewire 314 at a position beyond the distal end (or the projection 309) of the guidewire inserter 301.

Figure 24:
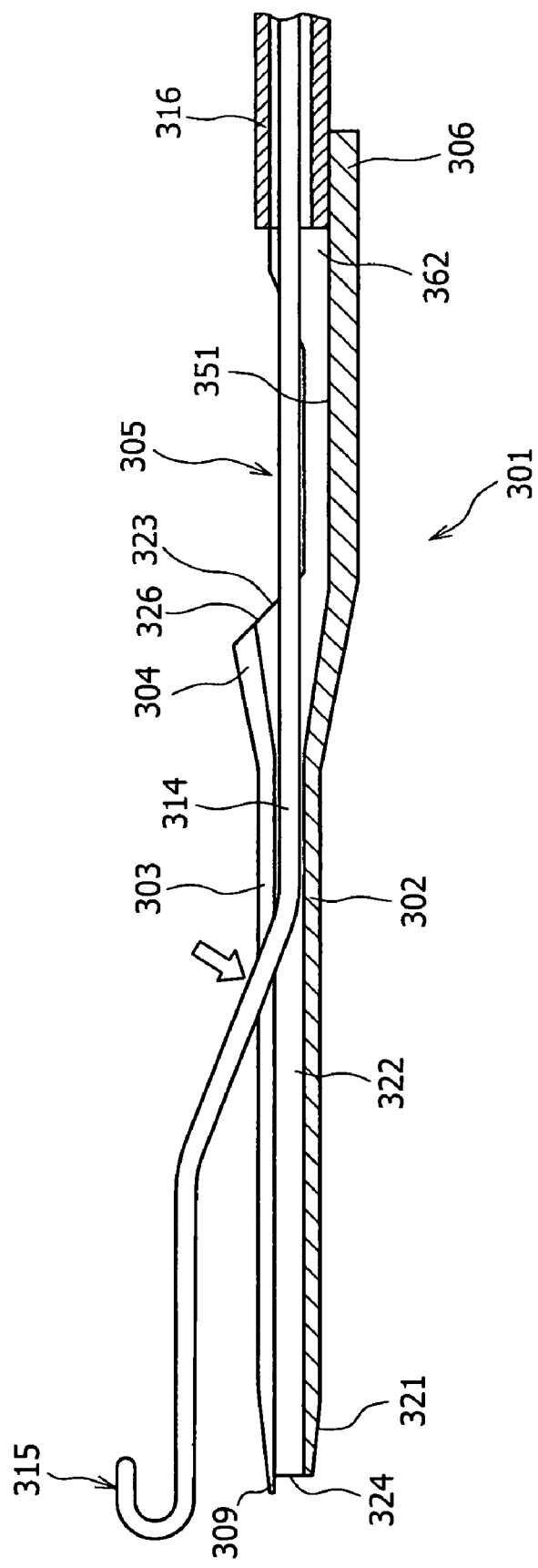
FIG. 24 is a sectional side view illustrating how to use the guidewire inserter according to the present invention.

Then, the portion in the aperture 304 of the guidewire 314 is push into the bore 322 (as indicated by an arrow in FIG. 23), thereby squeezing the guidewire 314 into the slit 303. The slit 303 is kept opened toward the distal end, thereby sequentially inserting the guidewire 314 into the bore 322, as shown in FIG. 24.

Figure 25:
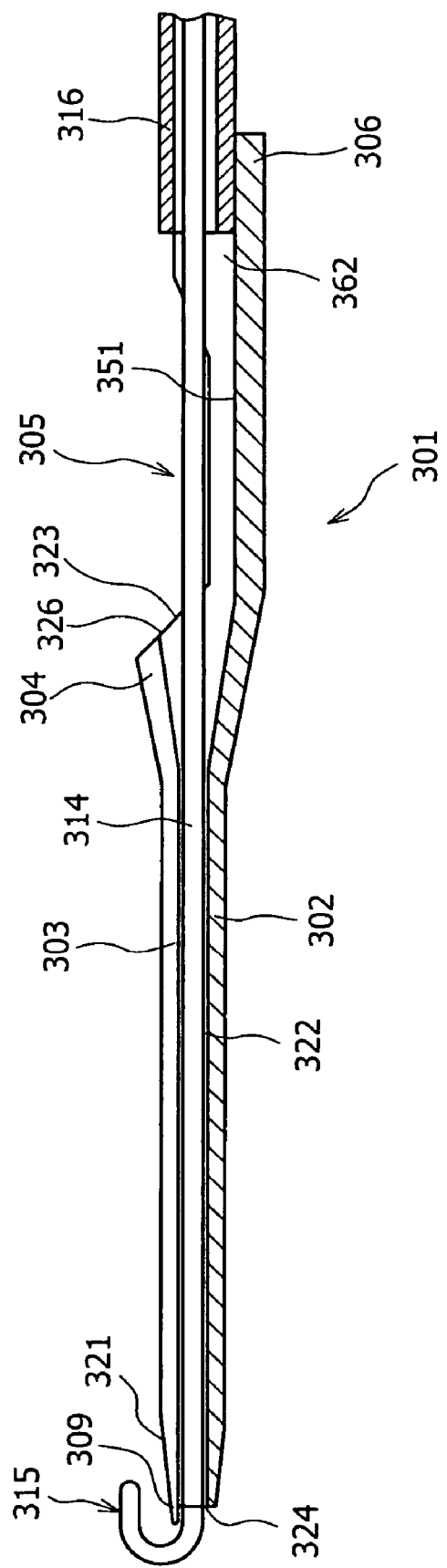
FIG. 25 is a sectional side view illustrating how to use the guidewire inserter according to the present invention.

The above-mentioned procedure is continued up to the distal end of the tubular member 302, thereby inserting the guidewire 314 into the bore 322, as shown in FIG. 25. In this state, the guidewire 314 passes through the inlet 323 and the bore 322 and projects in the distal direction from the outlet 324. The curved tip 315 of guidewire 314, which projects from the outlet 324, retains its curved shape.

Figure 26:
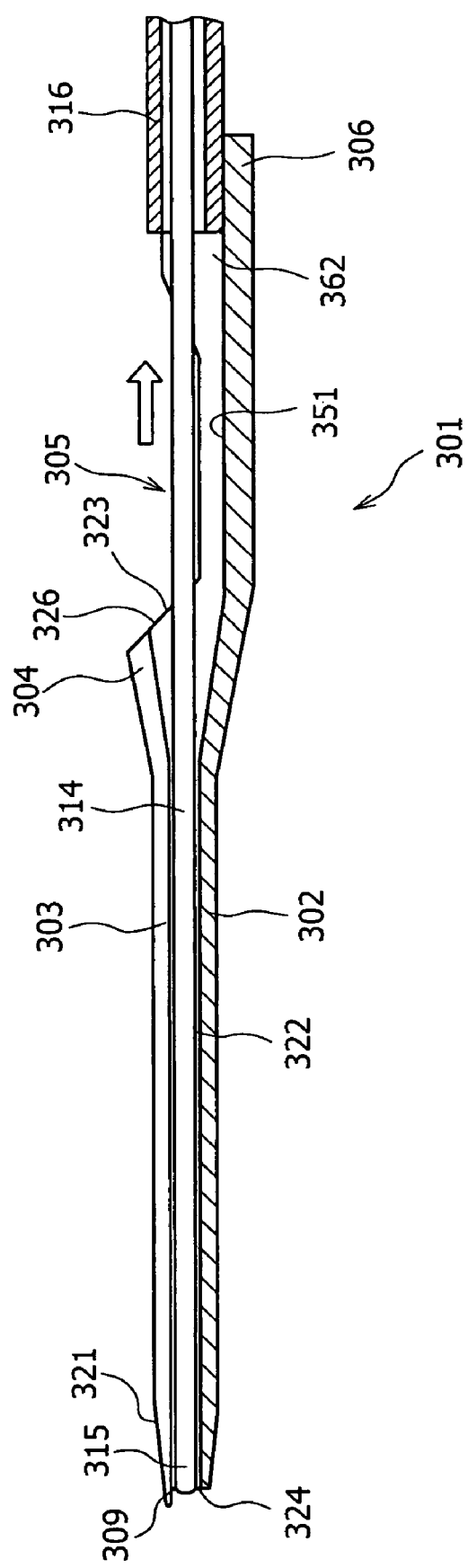
FIG. 26 is a sectional side view illustrating how to use the guidewire inserter according to the present invention.

In the next step shown in FIG. 26, the guidewire 314 is pulled toward the proximal end, so that the curved tip 315 is nearly straightened and put in the bore 322. This procedure is carried out by moving the guidewire 314 toward the proximal end, while pushing the guidewire 314 with the thumb finger against the internal surface 351 and holding the open part 305 and the protruded pieces 308 with one hand. During this procedure, the projection 309 at the distal end of the tubular member 302 prevents the curved tip 315 from being caught by the slit 303. In this way it is possible to straighten the curved tip of the guidewire 314 easily and certainly.

In the next step shown in FIG. 27, the distal end of the guidewire inserter 3b1 is inserted and connected into the bore of the hub 311 of the tube 310, while keeping the state shown in FIG. 26. To carry out this procedure, the guidewire inserter 301 is hold with one hand and the tube 310 with the other hand to move them toward each other.

The tapered part 321 is kept inserting into the hub 311 until the outermost surface 371 of the protruded pieces 307 come into close contact with the inside of the hub 311. (This procedure is possible because the inside of the hub 311 is tapered toward the distal end, and the outermost surface 371 of the protruded pieces 307 is sloped and convexly curved, as mentioned above.) In this state, the distal end of the guidewire inserter 301 is fitted and connected to the tube 310, as shown in FIG. 27. It is to be noted that the outlet 324 at the distal end of the tubular member 302 nearly coincides with the position of the proximal opening 313 (shaft entrance) of the catheter 312, and the center of the outlet 324 nearly coincides with the center of the proximal opening 313.

After the guidewire inserter 301 has been fitted and connected to the tube 310, the guidewire 314 is fed to distal in the same way as mentioned above, so that the guidewire projects from the outlet 324 and enters the catheter 312 of the tube 310. As described above, the outlet 324 of the tubular member 302 nearly coincides with the proximal opening 313 of the catheter 312 and the center of the outlet 324 nearly coincides with the center of the proximal opening 313. Therefore, the guidewire 314, which has projected from the outlet 324, enters the catheter 312 smoothly and certainly.

The advantage of this embodiment is that it is possible to connect the guidewire inserter 301 to the tube 310 and to feed the guidewire 314 into the catheter 312 easily and certainly because the curved tip 315 of the guidewire 314 is adequately straightened.

Fifth Embodiment

Figure 28:
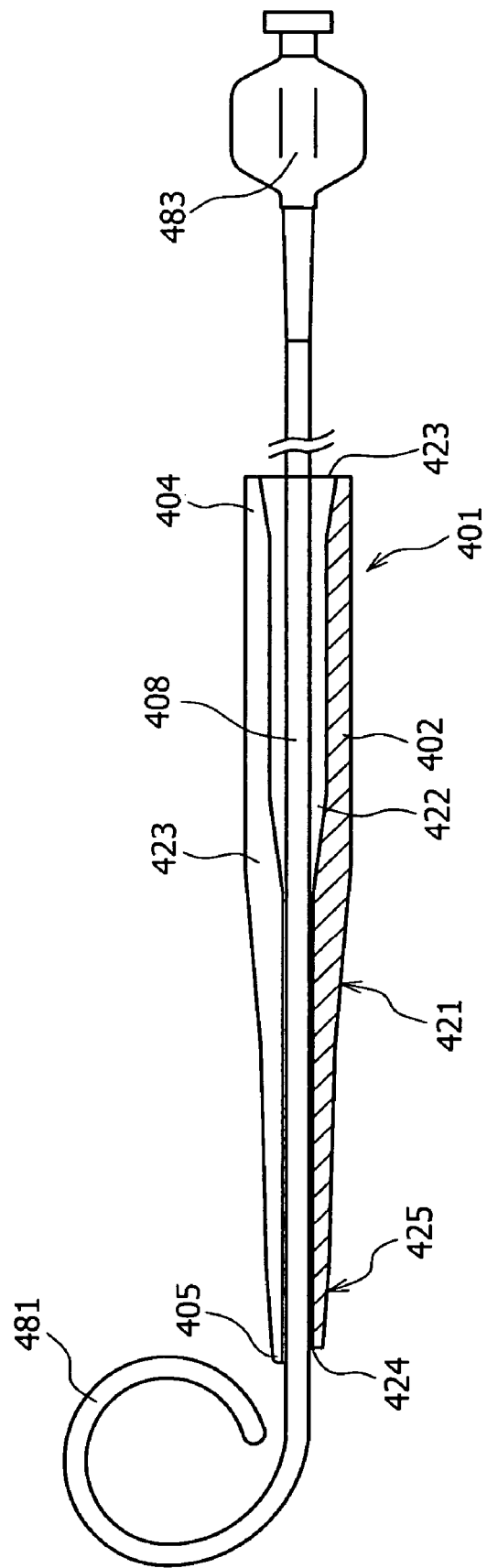
FIG. 28 is a sectional side view showing the device for introduction of a long item according to the fifth embodiment of the present invention, with the device being used as a catheter inserter.
Figure 29:
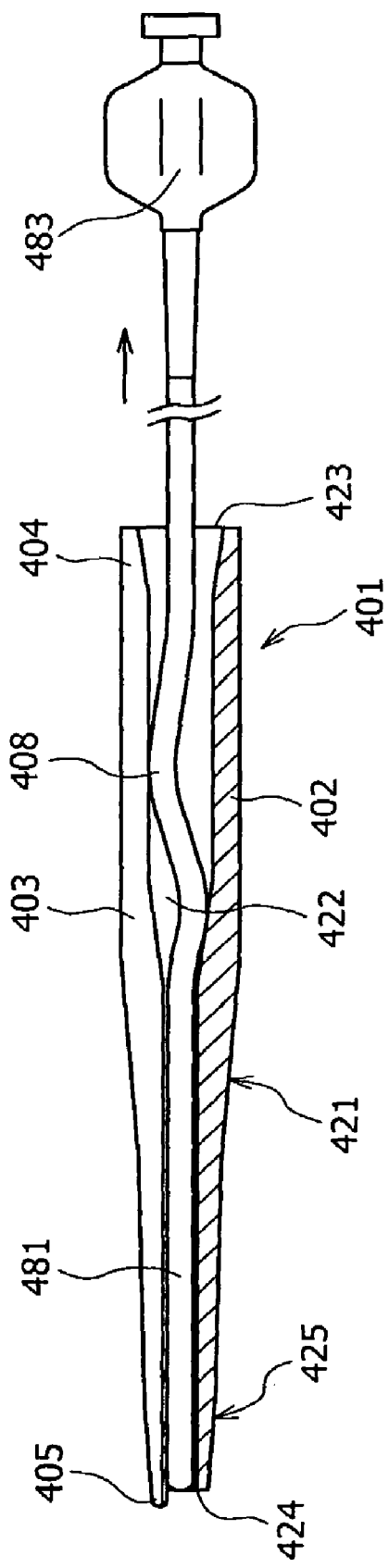
FIG. 29 is a sectional side view illustrating how to use the catheter inserter according to the present invention.
Figure 30:
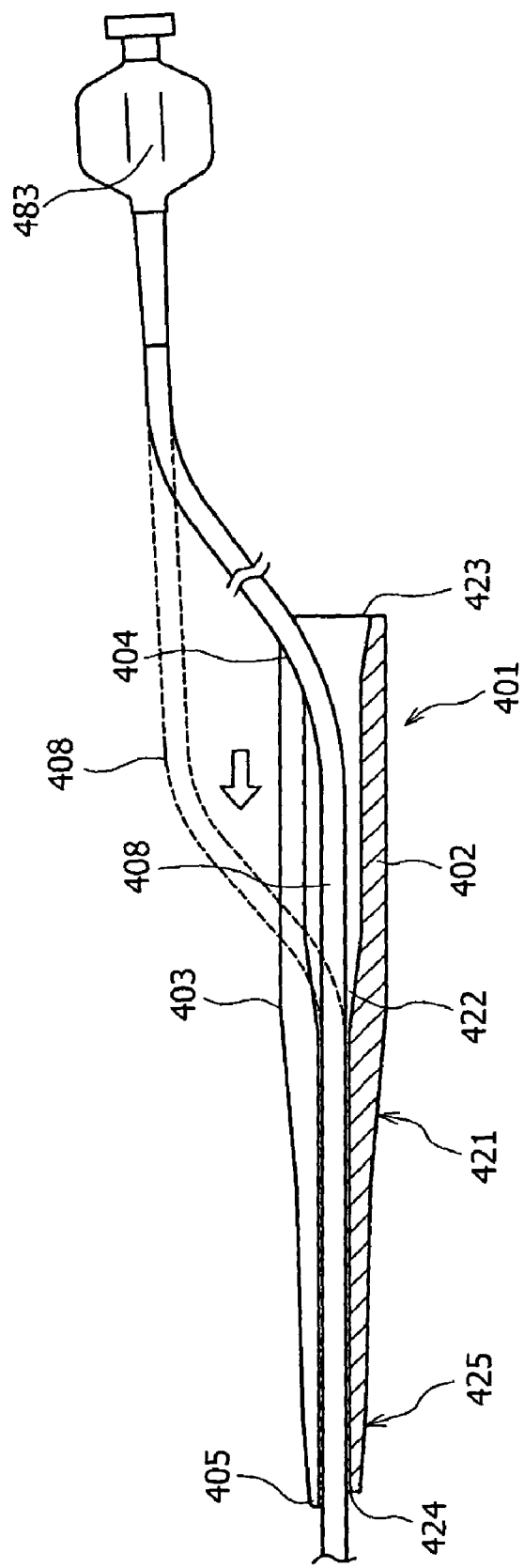
FIG. 30 is a sectional side view illustrating how to use the catheter inserter according to the present invention.

FIG. 28 is a sectional side view showing the device for introduction of a long item according to the fifth embodiment of the present invention. The device is used as a catheter inserter. FIG. 29 is a sectional side view illustrating how to use the catheter inserter according to the present invention (with the curved tip 418 of the catheter 408 inserted into the bore 422 and straightened). FIG. 30 is a sectional side view illustrating how to use the catheter inserter according to the present invention (with the catheter inserter 401 removed from the catheter 408). In what follows, the catheter inserter will be explained with reference to these drawings, with emphases placed on differences from the guidewire inserter explained in the first embodiment.

The catheter inserter 401 is a tubular member 402 similar to that mentioned above, which has therein a bore 422 (guidewire passage) that permits the catheter 408, which is the medical long item, to pass through. The tubular member 402 has a slit 403, an aperture 404, and a protruded part 405, as in the case mentioned above.

Incidentally, the tubular member 402 may have, on the sides of its distal end 425, a pair of protruded rims projecting in the mutually opposite directions from its central axis.

The tubular member 402 may also have, on the sides of its proximal end, a pair of wing-like protruded pieces, which project in the mutually opposite direction from the central axis of the catheter inserter 401.

In the illustrated case, the catheter 408 inserted into the bore 422 is an angiography catheter of pigtail type (having a curved tip 481 which is looped). This catheter 408 has a hub 483 at its proximal end.

The catheter inserter according to the present invention should be used in the following manner.

First, the catheter 408 is inserted into the aperture 404, while placing the curved tip 481 of the catheter 408 beyond the distal projection 405 of the catheter inserter 401.

Next, the part in the aperture 404 of the catheter 408 is pushed into the bore 422, thereby squeezing the catheter 408 into the slit 403. This procedure causes the slit 403 to gradually open toward the distal end and hence causes the catheter 408 to be sequentially inserted into the bore 422.

The foregoing procedure is continued up to the distal end of the tubular member 402, thereby inserting the catheter 408 completely into the bore 422, as shown in FIG. 28. In this stage, the catheter 408 passes through the inlet 423 and the bore 422 and projects from the distal end of the outlet 424. Then, the curved tip 481 of the catheter 408 projects from the distal end of the outlet 424 while keeping its looped shape.

Then, the catheter 408 is pulled toward the proximal end, thereby inserting the curved tip 481 into the bore 242. In this stage, the curved tip 481 is nearly straightened, as shown in FIG. 29. During this procedure, the projection 405 at the distal end of the tubular member 402 prevents the curved tip 481 from being caught by the slit 403. In this way it is possible to straighten the curved tip 481 of the catheter 408 easily and certainly.

The same effect as mentioned above will be produced for catheters of any type (for example, catheter of Jadkins type and catheter of Amplatz type), regardless of the shape of the curved tip 481 of the catheter 408.

The distal end 425 of the catheter inserter 401 is inserted and connected to the proximal end of the sheath and then the catheter 408 is fed to distal. In this way the catheter 408 is inserted into the sheath. Since the curved tip 481 of the catheter 408 has been straightened, the distal end 425 is easily and certainly connected to the sheath and the catheter 408 is fed easily and certainly into the sheath. In the case where the distal end 425 of the catheter inserter 401 is inserted into the proximal of the guidewire catching the blood vessel, the catheter 408 can be fed easily and certainly into the blood vessel.

There may be an instance in which the catheter 408 has to be removed from the catheter inserter 401, with catheter 408 left in the bore 422 of the catheter inserter 401. In this case, the procedure for removal is carried out as follows because the catheter 408 has the hub 483 at its proximal end.

As shown in FIG. 30, the catheter 408 is inserted into the aperture 404 and squeeze the catheter 408 into the slit 403 while pulling it out of the bore 422, so that the slit 403 gradually opens in going toward the distal end, thereby allowing the catheter 408 to be sequentially removed from the bore 422. (The removed catheter 408 is indicated by a dotted line in FIG. 30.)

Since the catheter inserter 401 according to this embodiment has the slit 403, which cuts across the wall of the tubular member 402 over the total length of the tubular member 402, it is possible to remove the catheter 408 from the catheter inserter 401 easily and rapidly.

Incidentally, the catheter to be inserted into the catheter inserter 401 is not limited to the angiography catheter mentioned above; but it includes catheters of any kind and use.

The embodiments mentioned above to illustrate the present invention are not intended to restrict the scope of the present invention. They may be modified by replacement with equivalent components or by addition of other components.

For example, the slit, which is straight in plan views of FIGS. 1, 8, 15, and 21, may be totally or partly curved or bent or zigzag.

The device for introduction of a long item, which is covered in the present invention, is not limited to the guidewire inserter and catheter inserter mentioned above. It includes any device to introduce a long item for medical use other than guidewire and catheter.

What is claimed is:

1. A catheter inserter combination comprising:
   a catheter comprising a curved tip;
   a tubular member having a wall and a bore for passage of the catheter, and only a single slit cutting completely through the wall of the tubular member over the entire length of the tubular member, wherein the tubular member comprises a projection at its distal end that projects distally beyond circumferentially adjacent portions of the tubular member, and the slit cuts completely through the wall of the projection.

2. The catheter inserter combination as defined in claim 1, wherein said projection possesses a mountain-like shape having a vertex and slopes in a plan view, and the slit cuts completely through the wall of the vertex or slope of the mountain-like shape.

3. The catheter inserter combination as defined in claim 1, wherein said tubular member has at its proximal end an aperture resulting from the slit expanding towards the proximal end.

4. A catheter inserter combination comprising:
   a catheter comprising a curved tip;
   a tubular member having a wall and a bore for passage of the catheter, only a single slit cutting completely through the wall of the tubular member over the entire length of the tubular member, the tubular member possessing a distal end portion, the distal end portion of the tubular member comprising a projection projecting distally beyond circumferentially adjacent portions of the tubular member so that the projection is a distalmost end of the tubular member, and the slit cutting through the wall of the projection so that an inner surface of the projection communicates with an outer surface of the projection by way of the slit.

5. A method comprising:
   positioning a catheter adjacent a tubular member so that at least a part of a distal end portion of the catheter extends distally beyond a distal end of the tubular member, the tubular member comprising a bore and a slit cutting completely through the wall of the tubular member over the total length of the tubular member;
   pushing the catheter through the slit in the wall of the tubular member so that the catheter enters the bore of the tubular member; and
   moving the catheter, located in the bore of the tubular member, relative to the tubular member so that the catheter moves toward a proximal end of the tubular member.

6. The method according to claim 5, wherein the catheter possesses a curved tip, and the positioning of the catheter comprises positioning the catheter so that the curved tip of the catheter extends distally beyond the distal end of the tubular member.

7. The method according to claim 5, wherein the catheter possesses a curved tip, and the moving of the catheter relative to the tubular member comprises moving the catheter relative to the tubular member to pull the curved tip of the catheter from a position entirely outside the bore to a position entirely inside the bore.

8. The method according to claim 5, wherein the catheter possesses a distal portion that is curved, and the moving of the catheter relative to the tubular member comprises moving the catheter relative to the tubular member to pull the distal portion of the catheter into the bore so that the curved portion of the catheter is straightened out as the distal portion is pulled into the bore.

9. The method according to claim 5, wherein the catheter is an angiographic catheter.

10. The method according to claim 5, wherein the catheter comprises a hub at a proximal end of the catheter.

* * * * *